US006107538A

United States Patent [19]
Young et al.

[11] Patent Number: 6,107,538
[45] Date of Patent: *Aug. 22, 2000

[54] ABSORBENT MEMBERS FOR ABSORBING BODY LIQUIDS

[75] Inventors: Gerald Alfred Young; Thomas Allen DesMarais, both of Cincinnati, Ohio; Gianfranco Palumbo, Bad Homburg; Mattias Schmidt, Idstein, both of Germany

[73] Assignee: The Procter & Gamble Company, Cincinnati, Ohio

[*] Notice: This patent is subject to a terminal disclaimer.

[21] Appl. No.: 09/042,435

[22] Filed: Mar. 13, 1998

Related U.S. Application Data

[60] Continuation-in-part of application No. 08/721,648, Sep. 26, 1996, Pat. No. 5,744,506, which is a division of application No. 08/655,041, May 28, 1996, Pat. No. 5,741,581, which is a division of application No. 08/563,866, Nov. 29, 1995, Pat. No. 5,650,222, which is a continuation of application No. 08/370,922, Jan. 10, 1995, abandoned.

[51] Int. Cl.$^7$ ...................................................... A61F 13/15

[52] U.S. Cl. ........................ 604/369; 604/368; 604/367; 604/385.1; 604/358

[58] Field of Search .................................. 604/369, 368, 604/367, 385.1, 358

[56] References Cited

U.S. PATENT DOCUMENTS

| | | | |
|---|---|---|---|
| 3,525,338 | 8/1970 | Bernardin | 128/290 |
| 4,381,783 | 5/1983 | Elias | 604/368 |
| 4,689,118 | 8/1987 | Makoui et al. | 162/100 |
| 4,737,582 | 4/1988 | Goldman et al. | 536/2 |
| 4,761,203 | 8/1988 | Vinson | 162/9 |
| 4,875,974 | 10/1989 | Rich | 162/10 |
| 4,923,454 | 5/1990 | Seymour et al. | 604/368 |
| 4,988,345 | 1/1991 | Reising . | |
| 5,350,370 | 9/1994 | Jackson et al. | 604/367 |
| 5,425,725 | 6/1995 | Tanzer et al. | 604/368 |
| 5,436,066 | 7/1995 | Chen | 604/358 |
| 5,454,910 | 10/1995 | Yoon et al. | 162/157.3 |

(List continued on next page.)

FOREIGN PATENT DOCUMENTS

| | | |
|---|---|---|
| 0 138 427 A2 | 4/1985 | European Pat. Off. ........ A61F 13/18 |
| 2649974 | 5/1977 | Germany . |
| WO 93/04092 | 3/1993 | WIPO . |
| WO 95/13777 | 5/1995 | WIPO . |
| WO 96/21681 | 7/1996 | WIPO . |
| WO 98/22065 | 5/1998 | WIPO . |
| WO 98/22067 | 5/1998 | WIPO . |

OTHER PUBLICATIONS

International Search Report Dated Jun. 16, 1999.
"Enhanced Fluid Transport in Absorbent Structures Through Use of Superabsorbent Fibrids" by William T. Ryans, Hoechst Celanese Corporation, Charlotte, NC—International Nonwovens Journal, 6, No. 3, 50–53, summer 1994.
Ryans, W.T. et al., "Enhanced Fluid Transport in Absorbent Products Through Use of Superabsorbent Fibrid Structures", Hoescst Celanese Corporation, Charlotte, NC, pp. 1–9 (no date available).

*Primary Examiner*—John G. Weiss
*Assistant Examiner*—Miley Craig Peppers, III
*Attorney, Agent, or Firm*—Carl J. Roof; Kevin D. Hogg; Kirsten K. Stone

[57] ABSTRACT

Described are absorbent members useful in the containment of body liquids such as urine. The storage members have a high capillary suction capacity. For purposes of the present disclosure, capillary suction capacity is measured in terms of the member's ability to uptake liquid at relatively high capillary pressures, which are generally encountered when the member is positioned in an absorbent article. In particular, capillary suction capacity is measured in terms of a member's capillary sorption absorbent capacity, which is measured in accordance with the Capillary Sorption method described in the Test Methods section of the disclosure. The absorbent members may include an osmotic absorbent (preferably a hydrogel-forming absorbent polymer) or a high surface area material, or a combination thereof.

53 Claims, 8 Drawing Sheets

U.S. PATENT DOCUMENTS

| | | | |
|---|---|---|---|
| 5,462,538 | 10/1995 | Korpman | 604/372 |
| 5,387,207 | 2/1995 | Dyer et al. | 604/369 |
| 5,466,232 | 11/1995 | Cadieux et al. | 604/378 |
| 5,486,410 | 1/1996 | Groeger et al. | 428/283 |
| 5,506,035 | 4/1996 | Van Phan et al. | 428/196 |
| 5,536,264 | 7/1996 | Hsueh et al. | 604/368 |
| 5,560,878 | 10/1996 | Dragoo et al. | 264/115 |
| 5,580,348 | 12/1996 | Blaney et al. | 604/367 |
| 5,650,222 | 7/1997 | DesMarais et al. . | |
| 5,651,862 | 7/1997 | Anderson et al. | 162/127 |
| 5,744,506 | 4/1998 | Goldman et al. . | |
| 5,900,437 | 5/1999 | Mitchell et al. . | |

ABSORBENT MEMBERS FOR ABSORBING BODY LIQUIDS

CROSS REFERENCE TO RELATED APPLICATIONS

This application is a continuation-in-part of U.S. patent application Ser. No. 08/721,648 (Goldman et al.), filed Sep. 26, 1996, now U.S. Pat. No. 5,744,506, which is a divisional of U.S. patent application Ser. No. 08/655,041 (DesMarais et al.), filed May 28, 1996, now U.S. Pat. No. 5,741,581, which is a divisional of U.S. patent application Ser. No. 08/563,866 (DesMarais et al.), filed Nov. 29, 1995 (now U.S. Pat. No. 5,650,222), which is a continuation of U.S. patent application Ser. No. 08/370,922 (DesMarais et al.), filed Jan. 10, 1995 (now abandoned). Applicants claim priority to these applications, pursuant to 35 U.S.C. §120.

TECHNICAL FIELD

This application relates to absorbent members for body liquids such as urine and menses. This application particularly relates to absorbent members having high capillary suction properties.

BACKGROUND OF THE INVENTION

The development of highly absorbent member, for use as disposable diapers, adult incontinence pads and briefs, and catamenial products such as sanitary napkins, are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body liquids, in particular urine. In this regard, the use of certain absorbent polymers often referred to as "hydrogels," "superabsorbents" or "hydrocolloid" material has been particularly important. See, for example, U.S. Pat. No. 3,669,103 (Harper et al.), issued Jun. 13, 1972, and U.S. Pat. No. 3,670,731 (Harmon), issued Jun. 20, 1972, that disclose the use of such absorbent polymers (hereafter referred to as "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged body liquids, typically when used in combination with a fibrous matrix. See, for example, U.S. Pat. No. 4,673,402 (Weisman et al.), issued Jun. 16, 1987 and U.S. Pat. No. 4,935,022 (Lash et al.), issued Jun. 19, 1990, that disclose dual-layer core structures comprising a fibrous matrix and hydrogel-forming absorbent polymers useful in fashioning thin, compact, nonbulky diapers. See also, U.S. Pat. No. 5,562,646 (Goldman et al.), issued Oct. 8, 1996 and U.S. Pat. No. 5,599,335 (Goldman et al.), issued Feb. 4, 1997, both of which relate to absorbent cores comprising regions of high concentrations of hydrogel-forming polymer, where the polymer forms a gel-continuous liquid transportation zone upon swelling.

In addition to the use of hydrogel-forming absorbent polymers as the primary component in absorbent article storage structures, the use of polymeric foam materials derived from high internal phase water-in-oil emulsions ("HIPEs") has been identified. See, e.g., U.S. Pat. No. 5,260,345 (DesMarais et al.), issued Nov. 9, 1993, U.S. Pat. No. 5,387,207 (Dyer et al.) issued Feb. 7, 1995, and U.S. Pat. No. 5,560,222 (DesMarais et al.), issued Jul. 22, 1997. The foam materials, particularly those designed to function as liquid storage/redistribution components, provide several advantages over is storage structures comprising hydrogel-forming absorbent polymers in a fibrous matrix, including good wicking and liquid distribution characteristics, high storage capacity under pressure, flexibility, etc.

The primary focus of prior work in both the hydrogel-forming absorbent polymer and HIPE foam areas has been the maximization of liquid storage capacity in a relatively thin material. Hydrogel-forming absorbent polymer materials absorb liquid and provide a leakage protection and dryness in absorbent products. Once absorbed, the liquid in absorbent polymers is tightly held by osmotic forces, which helps prevent rewet of the topsheet by previously absorbed urine. However, hydrogel-forming polymer by itself has little ability to absorb liquid if the liquid is not delivered to its surface. This is especially critical at high capillary heights where the liquid is present only in small capillaries. For example, conventional softwood pulp exhibits almost no uptake at capillary suction heights of 100 cm. It is not surprising, then, that a mixture of pulp and hydrogel-forming polymer exhibits almost no uptake at 100 cm. Thus, in spite of the advancements made to achieve the goal of high liquid storage capacity in thin materials, there is a continuing need to provide high storage capacity materials that also exhibit high capillary suction capabilities. Storage materials which exhibit high capillary suction capacity will allow the dewatering of other absorbent core materials such as acquisition and distribution materials, one or both of which are typically included in absorbent cores of absorbent articles. By thoroughly dewatering these other absorbent core components, those materials will be better able to handle additional insults of liquid by the wearer. In addition to high capillary suction capacities in general, a particularly desirable property is the ability to provide such capacities at relatively high capillary suction heights. Movement of liquid from the discharge region (i.e., the crotch region of the article) to the front and rear of the article may provide enhanced wearer comfort when the article is wetted with liquid. As is clear, the ability of a storage material to dewater other core components, particularly the distribution material that wicks liquid to high capillary heights, is particularly relevant to their functioning as absorbent materials in absorbent articles.

Accordingly, it would be desirable to be able to provide a storage absorbent member having a high capillary suction capacity, wherein the storage absorbent member comprises hydrogel-forming absorbent polymer or another material that absorbs liquids primarily as a result of osmotic forces.

SUMMARY OF THE INVENTION

The present invention relates to absorbent members useful in the containment (e.g., storage) of body liquids such as urine. These storage absorbent members have a high capillary suction capacity. For purposes of the present disclosure, capillary suction capacity is measured in terms of the member's ability to uptake liquid at relatively high capillary pressures, which are generally encountered when the member is positioned in an absorbent article. In particular, capillary suction capacity is measured in terms of a members capillary sorption absorbent capacity, which is measured in accordance with the Capillary Sorption method described in the Test Methods section below.

DETAILED DESCRIPTION OF THE INVENTION

I. Definitions

Figure 1:
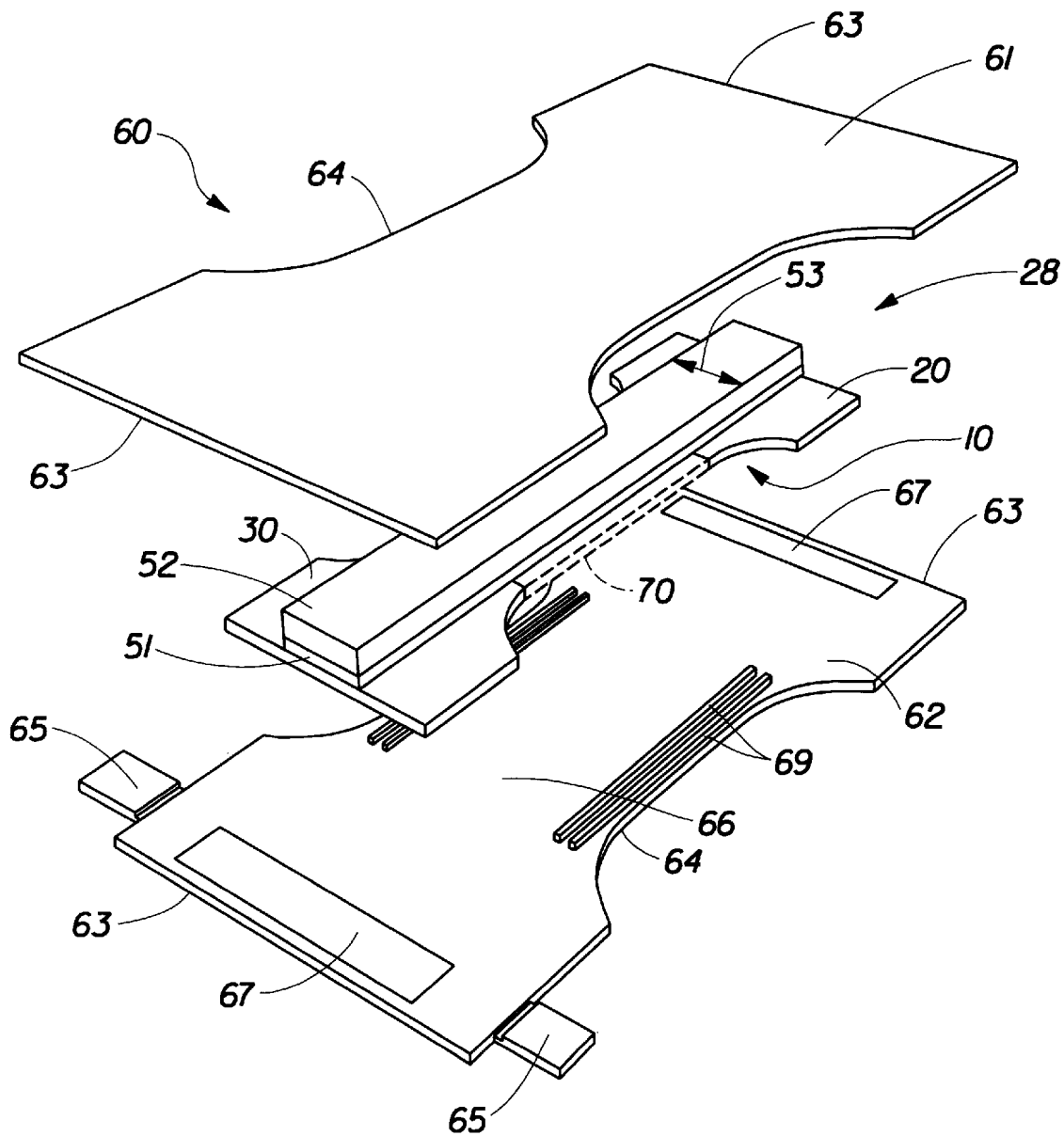
FIG. 1 of the drawings is a blown-apart view of a diaper having an absorbent core which comprises a high capillary suction capacity storage absorbent member of the present invention.

As used herein, the term "body liquids" includes, but is not limited to, urine, menses, vaginal discharges, sweat and feces.

As used herein, the term "absorbent core" refers to the component of the absorbent article that is primarily responsible for liquid hand ling properties of the article, including acquiring, transporting, distributing and storing body liquids. As such, the absorbent core typically does not include the topsheet or backsheet of the absorbent article.

As used herein, the term "absorbent member" refers to the components of the absorbent core that typically provide one or more liquid handling properties, e.g., liquid acquisition, liquid distribution, liquid transportation, liquid storage, etc. The absorbent member can comprise the entire absorbent core or only a portion of the absorbent core, i.e., the absorbent core can comprise one or more absorbent members. The "storage absorbent member" is the absorbent member component(s) of the absorbent core that functions primarily to store absorbed liquids. As discussed above, the storage absorbent member may also function distribute liquid as a result of its vertical wicking capability.

As use herein, the term "layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered."

As used herein, the term "osmotic absorbent" refers to a material or structure that absorbs solution in response to a chemical potential difference between absorbed and non-absorbed solutions. Generally, this chemical potential difference arises from a higher solute concentration for the absorbed solution. In order to inhibit equalization of solute concentration via diffusion of solute species, an osmotic absorbent typically has a diffusion barrier that selectively inhibits the diffusion of at least one solute species. Examples of suitable diffusion barriers are (i) a semi-permeable reverse-osmosis membrane, wherein the membrane provides a diffusion barrier to soluble salts (e.g., NaCl) and (ii) a crosslinked polyelectrolyte network (e.g., used in hydrogels), wherein the polyelectrolyte network retains dissociated counterions inside the gel as a result of electroneutrality considerations. Examples of osmotic packet or chamber absorbents are described in U.S. Pat. No. 5,108,383 issued Apr. 28, 1992 to White and U.S. Pat. No. 5,082,723 issued Jan. 21, 1992 to Gross et al., the disclosure of each of which is incorporated herein by reference. A particularly preferred osmotic absorbent for use in the storage absorbent members of the present invention are hydrogel-forming absorbent polymers, which are described in detail below.

As used herein, the term "X-Y dimension" refers to the plane orthogonal to the thickness of the member, core or article. The X-Y dimension usually corresponds to the length and width, respectively, of the member, core or article.

As used herein, the terms "region(s)" or "zone(s)" refer to portions or sections of S the absorbent member.

As used herein, the term "Z-dimension" refers to the dimension orthogonal to the length and width of the member, core or article. The Z-dimension usually corresponds to the thickness of the member, core or article.

For purposes of this invention, it should also be understood that the term "upper" refers to absorbent members, such as layers, that are nearest to the wearer of the absorbent article, and typically are relatively proximate the topsheet of an absorbent article; conversely, the term "lower" refers to absorbent members that are furthermost away from the wearer of the absorbent article and typically are more proximate the backsheet.

As used herein, the term "comprising" means various components, members, steps and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios and proportions used herein are by weight unless otherwise specified.

II. Capillary Suction Properties of the Storage Absorbent Member

The storage absorbent members of the present invention exhibit high capillary suction capacities. For purposes of the present disclosure this high suction capacity is measured in terms of the member's ability to uptake liquid at high capillary heights, which are generally encountered when the member is positioned in an absorbent article. The Capillary Sorption Absorbent Capacity test (also referred to herein as the Capillary Sorption test) measures the amount of test liquid per gram of storage absorbent member that is taken up when the storage member is placed at varying heights on a capillary sorption apparatus. The Capillary Sorption Absorbent Capacity test is described in greater detail in the Test Methods section below. Capillary sorption absorbent capacity data for certain materials is set forth in Table 1 below. In particular, capillary sorption absorbent capacity data are provided for: (i) a storage absorbent member consisting of high surface area glass microfibers and particles of hydrogel-forming absorbent polymer (made according to Example 1 below); (ii) a storage absorbent member consisting of a high surface area polymeric foam (made according to Example 3 below); (iii) a storage absorbent member consisting of particles of high surface area polymeric foam and particles of hydrogel-forming absorbent polymer (made according to Example 5 below); and (iv) a storage absorbent member consisting of high surface area cellulose acetate fibrets and particles of hydrogel-forming absorbent polymer (made according to Example 6 below). Capillary sorption absorbent capacity data for materials representative of the prior art (designated as Comparative A and Comparative B) are also depicted in Table 1. Prior art sample Comparative A was a 5.4 cm circular-shaped structure punched from a member (see discussion below) comprising a blend of cellulose fluff (Flint River Pulp from Weyerhauser Co., Washington), approximately 42% by weight, and hydrogel-forming absorbent polymer (available from Clariant GmbH, Frank-furt, Germany as IM 7300), approximately 58% by weight. Prior art sample Comparative B is a polymeric foam material prepared according to U.S. Pat. No. 5,650,222, issued to DesMarais et al.

In one aspect, the high capillary suction capacity storage absorbent member of the present invention has a capillary sorption absorbent capacity at a height of 35 cm of at least about 12 g/g, preferably at least about 14 g/g, more preferably at least about 20 g/g, still more preferably at least about 27 g/g. Typically, these storage absorbent members will have a capillary sorption absorbent capacity at a height of 35 cm of from about 12 g/g to about 60 g/g, more typically from about 14 g/g to about 50 g/g, more typically from about 20 g/g to about 40 g/g.

In another aspect, the high capillary suction capacity storage absorbent material has a capillary sorption absorbent capacity at a height of 70 cm of at least about 7 g/g, preferably at least about 9 g/g, more preferably at least about 11 g/g, still more preferably at least about 14 g/g. Typically, these storage absorbent members will have a capillary sorption absorbent capacity at a height of 70 cm of from about 7 g/g to about 35 g/g, more typically from about 9 g/g to about 30 g/g, still more typically from about 11 g/g to about 25 g/g.

In yet another aspect, the high capillary suction capacity storage absorbent material has a capillary sorption absorbent capacity at a height of 120 cm of at least about 4 g/g, preferably at least about 5 g/g, more preferably ai least about 7 g/g, still more preferably at least about 11 g/g. Typically, these storage absorbent members will have a capillary sorption absorbent capacity at a height of 120 cnm of from about 4 g/g to about 29 g/g, more typically from about 5 g/g to about 24 g/g, still more typically from about 7 g/g to about 19 g/g.

In yet another aspect, the high capillary suction capacity storage absorbent material has a capillary sorption absorbent capacity at a height of 200 cm of at least about 3 g/g, preferably at least about 4 g/g, more preferably at least about 6 g/g, still more preferably at least about 8 g/g. Typically, these storage absorbent members will have a capillary sorption absorbent capacity at a height of 200 cm of from about 3 g/g to about 25 g/g, more typically from about 4 g/g to about 20 g/g, still more typically from about 6 g/g to about 15 g/g.

With respect to storage absorbent members comprising osmotic absorbents and high surface area materials, in addition, or alternative, to defining the high suction capabilities of the present members in terms of capillary sorption absorbent capacity, particularly preferred members, e.g. those where the high surface area material is a polymeric foam, may be characterized by the member's ability to initially uptake liquid at high heights at relatively fast rates. High suction members that exhibit both high uptake at high suction and high initial effective uptake rates should provide superior user dryness as the extent of partitioning from other absorbent core members (e.g., acquisition or distribution materials) and its rate will be favorably improved by the high suction material. For purposes of the present disclosure, this latter property is referred to herein as the member's "initial effective uptake rate at 200 cm capillary suction height" (referred to herein as "initial effective uptake rate at 200 cm"), which is reported in units of g/g/hour. The initial effective uptake rate of a storage absorbent member is calculated by dividing the capillary suction absorbent capacity at 200 cm, by the time spent at 200 cm. Capillary suction absorbent capacity and time are readily determined using the Capillary Sorption method discussed in detail in the Test Methods section below. Though not a requirement, particularly preferred storage absorbent members will have an initial effective uptake rate at 200 cm of at least about 3 g/g/hr, more preferably at least about 4 g/g/hr, and most preferably at least about 8 g/g/hr. Typically, the effective uptake rate at 200 cm will be from about 3 to about 15 g/g/hr, more typically from about 4 to about 12 g/g/hr, still more typically from about 8 to about 12 g/g/hr.

While the above minimum capillary sorption absorbent capacities are important to the absorbent members of the present invention, the members will also preferably, though not necessarily, have a capillary sorption absorbent capacity at zero head pressure (i.e., at 0 cm in the Capillary Sorption test) of at least about 15 g/g. In another preferred aspect, the absorbent members will concurrently exhibit the required g/g uptake at at least two suction heights discussed above. That is, for example, preferred storage absorbent members will have 2 or more of the following properties: (i) a capillary sorption absorbent capacity at a height of 35 cm of at least about 12 g/g, preferably at least about 14 g/g, more preferably at least about 20 g/g, still more preferably at least about 27 g/g, (ii) a capillary sorption absorbent capacity at a height of 70 cm of at least about 7 g/g, preferably at least about 9 g/g, more preferably at least about 11 g/g, still more preferably at least about 14 g/g; (iii) a capillary sorption absorbent capacity at a height of 120 cm of at least about 4 g/g, preferably at least about 5 g/g, more preferably at least about 7 g/g, still more preferably at least about 11 g/g; (iv) a capillary sorption absorbent capacity at a height of 200 cm of at least about 3 g/g, preferably at least about 4 g/g, more preferably at least about 6 g/g, still more preferably at least about 8 g/g.

In yet another aspect, storage absorbent members of the present invention can be characterized in terms of exhibiting a relatively high absorbency efficiency (hereafter referred to as "capillary absorption efficiency") at various heights, relative to the material's capacity at zero head pressure. Capillary absorption efficiency at a given suction height is determined by dividing the capillary suction absorbent capacity of the material at that given height by the capillary suction absorbent capacity of that material at zero head pressure, i.e., 0 cm. In this regard, in one aspect, the absorbent member will have a capillary sorption absorbent capacity at zero height of at least about 15 g/g, preferably at least about 20 g/g, more preferably at least about 40 g/g and most preferably about 60 g/g, and capillary absorption efficiency at a height of 120 cm of at least about 25%, preferably at least about 30%, still more preferably at least about 40%. In another aspect, the absorbent member will have a capillary sorption absorbent capacity at zero height of at least about 15 g/g, preferably at least about 20 g/g, more preferably at least about 40 g/g and most preferably at least about 60 g/g, and a capillary absorption efficiency at a height of 70 cm of at least about 30%, preferably at least about 40%, still more preferably at least about 65%. In still another aspect, the absorbent member will have a capillary sorption absorbent capacity at zero height of at least about 15 g/g, preferably about 20g/g, more preferably about 40 g/g and most preferably about 60 g/g, and a capillary absorption efficiency at a height of 35 cm of at least about 50%, preferably at least about 70%, still more preferably at least about 90%.

In another aspect, preferred storage absorbent members of the present invention will have a relatively high medium absorption height, which is defined as the height at which the member has a capillary sorption absorbent capacity that is 50% of the capillary sorption absorbent capacity at 0 cm height. In this regard, preferred storage absorbent members will have a capillary sorption absorbent capacity at zero height of at least about 15 g/g, preferably at least about 20 g/g, more preferably at least about 40 g/g and most preferably about 60 g/g, and a medium absorption height of at least about 35 cm, more preferably at least about 40 cm, still more preferably at least about 50 cm, most preferably at least about 60 cm.

III. Components of the High Suction Storage Absorbent Members

Representative materials useful in preparing the storage absorbent members of the present invention are described in detail below. In one preferred embodiment, the storage absorbent member will be in the form of a high surface area hydrophilic polymeric foam. In another particularly preferred embodiment, the storage absorbent member will be in the form of a high surface area hydrophilic polymeric foam in combination with an osmotic absorbent material (e.g., a hydrogel-forming absorbent polymer). In yet another embodiment, the storage absorbent member will comprise a blend of high surface area fibers and an osmotic absorbent (e.g., a hydrogel-forming absorbent polymer).

A. High Surface Area Hydrophilic Polymeric Foams

As indicated, high surface area hydrophilic polymeric foams having high capillary suction capacities may be used as the primary component of the storage absorbent member, or such foams may be used in combination with an osmotic absorbent material. While the foams useful as the primary storage material (i.e., no additional materials which contribute significant absorbent capacity are used) will have many similar properties to foams that are used in combination with osmotic absorbents, there are certain foam properties that will vary depending on the specific embodiment in question. In this regard, in the discussion of specific foam properties below, where no distinction is made between foams useful as the primary storage absorbent component and those to be used in combination with an osmotic absorbent, it should be assumed the description of that foam property is applicable to both embodiments. In contrast, where different foam properties are applicable depending on the embodiment in question, descriptions for each embodiment are provided.

To the extent high surface area polymeric foams useful herein are described in terms of their physical properties, it may be necessary to perform analysis on the foam in sheet form. Thus, insofar as a foam is used in particulate form and is prepared from a previously formed sheet, physical property measurements will be conducted on the sheet foam (i.e., prior to forming particulates). Where the foam is formed in situ into particles (or beads) during the polymerization process, a similar foam (in terms of chemical composition, cell size, W:O ratio, etc.) can be formed into sheets for the purpose of making such measurements.

(1) General Polymeric Foam Characteristics

High surface area polymeric foams useful in the high capillary suction storage absorbent members comprising osmotic absorbents (e.g., hydrogel-forming absorbent polymer) of the present invention are known in the art. Particularly preferred foams for use in combination with osmotic absorbents are those obtained by polymerizing a high internal phase water-in-oil emulsion, such as those described in U.S. Pat. No. 5,387,207 and U.S. Pat. No. 5,650,222. Other particularly preferred polymeric foams which may be used alone or in combination with an osmotic absorbent are described in detail in co-pending U.S. patent application Ser. No. 09/042,429, filed Mar. 13, 1998 by T. DesMarais titled "HIGH SUCTION POLYMERIC FOAM MATERIALS" (P&G Case 7052) and co-pending U.S. patent application Ser. No. 09/042,418, filed Mar. 13, 1998 by T. DesMarais et al. titled "ABSORBENT MATERIALS FOR DISTRIBUTING AQUEOUS LIQUIDS" (P&G Case 7051), the disclosure of each of which is incorporated by reference herein. (Specific preferred foams described in one or both of these co-pending applications are described in the Examples section below.)

Polymeric foams useful herein are those which are relatively open-celled. This means many of the individual cells of the foam are in unobstructed communication with adjoining cells. The cells in such relatively open-celled foam structures have intercellular openings or "windows" that are large enough to permit ready liquid transfer from one cell to the other within the foam structure.

These relatively open-celled foam structures will generally have a reticulated character with the individual cells being defined by a plurality of mutually connected, three dimensionally branched webs. The strands of polymeric material making up these branched webs can be referred to as "struts." For purposes of the present invention, a most preferred foam material will have at least about 80% of the cells in the foam structure that are at least 1 $\mu$m in size in liquid communication with at least one adjacent cell.

In addition to being open-celled, these polymeric foams are sufficiently hydrophilic to permit the foam to absorb aqueous liquids. The internal surfaces of the foam structures are rendered hydrophilic by residual hydrophilizing surfactants left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area Such a procedure is described in greater detail in the Test Methods section of U.S. Pat. No. 5,387,207, infra. Foams which are useful high surface area materials in the present invention are generally those which exhibit an adhesion tension value of from about 15 to about 65 dynes/cm, more preferably from about 20 to about 65 dynes/cm, as determined by capillary absorption of synthetic urine having a surface tension of 65±5 dynes/cm.

The polymeric foams useful herein are preferably prepared in the form of collapsed (i.e., unexpanded), polymeric foams that, upon contact with aqueous liquids, absorb such liquids and expand when the amount absorbed lowers the combined capillary pressure plus confining pressure to below the expansion pressure (described below) of the foam. These collapsed polymeric foams are usually obtained by expressing the water phase from the polymerized HIPE foam through compressive forces, and/or thermal drying and/or vacuum dewatering. After compression, and/or thermal drying/vacuum dewatering, these polymeric foams are in a collapsed, or unexpanded state.

Figure 2A:
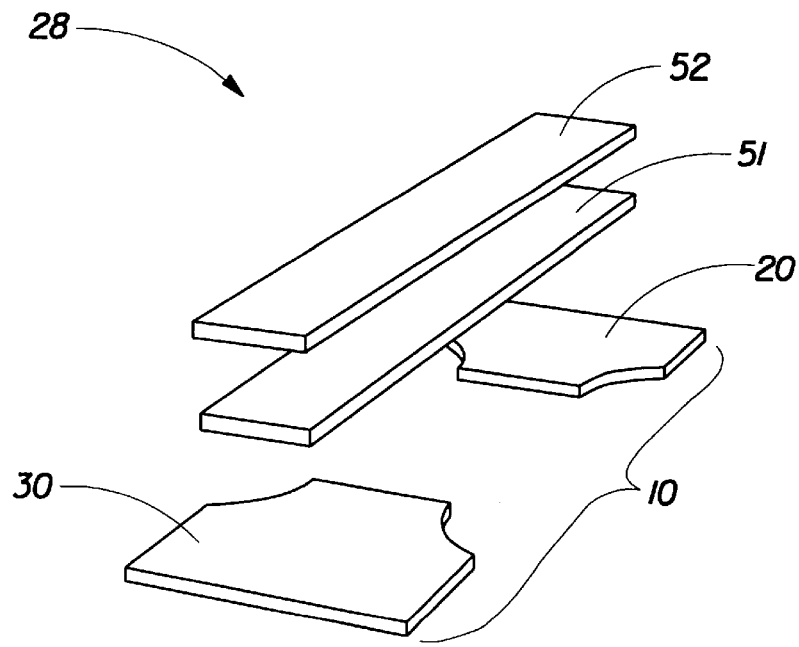
FIG. 2a of the drawings is a blown-apart view of a representative multi-layer core for inclusion in a diaper such as that shown in FIG. 1.
Figure 2B:
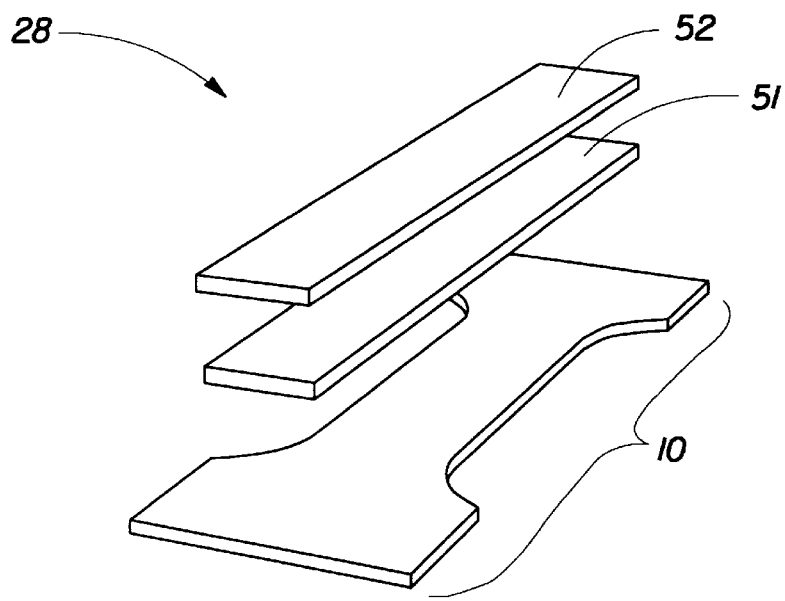
FIG. 2b of the drawings is a blown-apart view of another representative multi-layer core for inclusion in a diaper shown such as that shown in FIG. 1.
Figure 3:
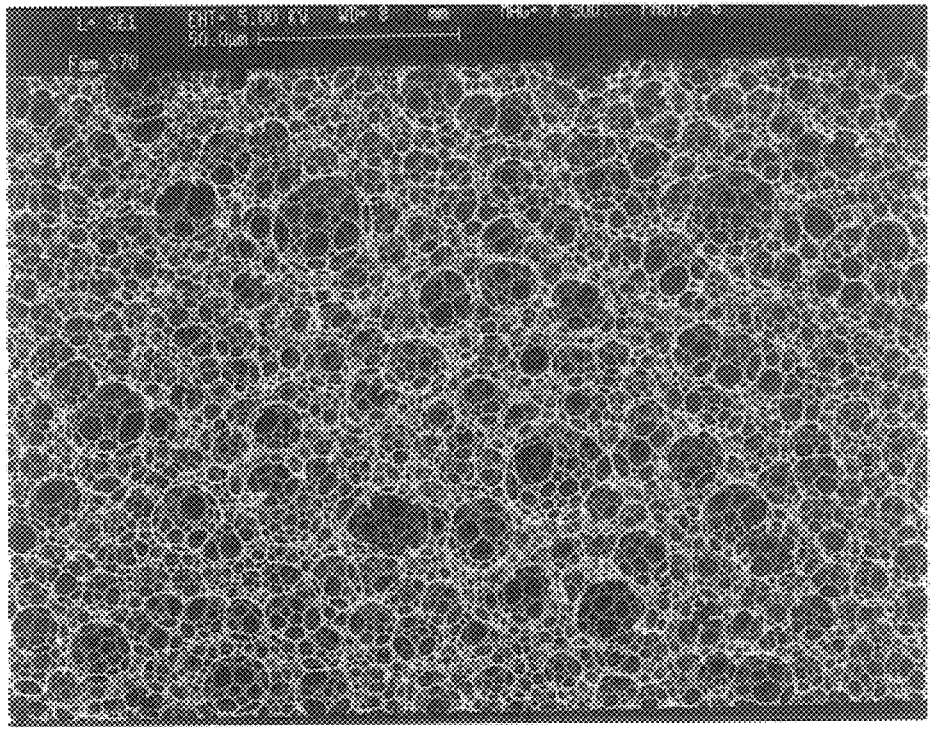
FIG. 3 is a photomicrograph (500× magnification) of a representative high surface area polymeric foam useful in the storage absorbent members of the present invention.
Figure 4:
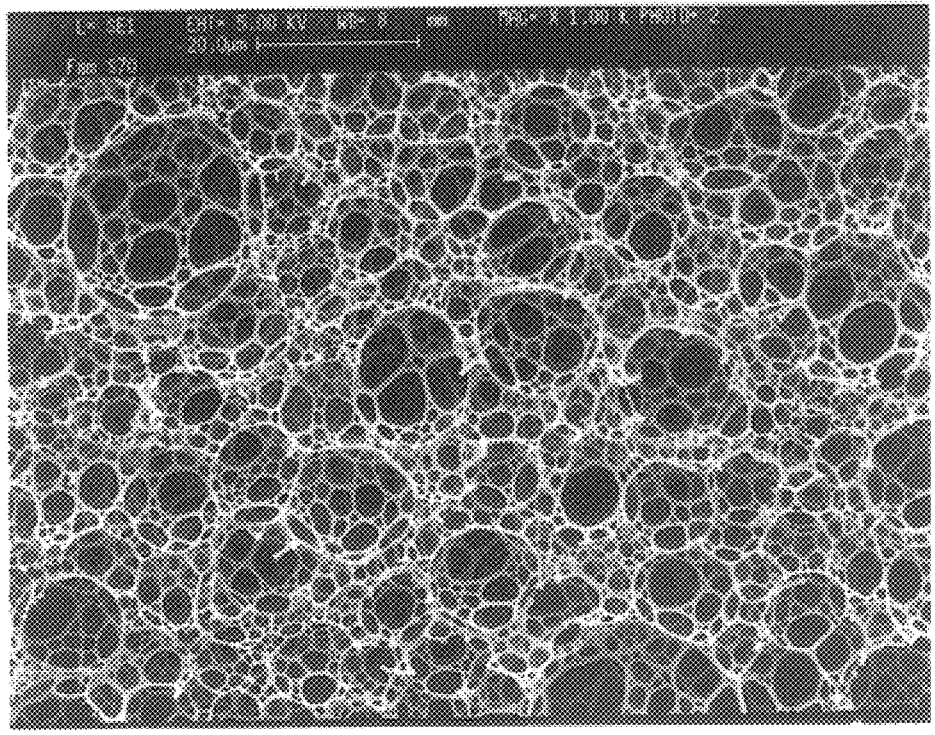
FIG. 4 is a photomicrograph the high surface area polymeric foam depicted in FIG. 3, except at 1000× magnification.

The cellular structure of a representative collapsed HIPE foam from which water has been expressed by compression is shown in the photomicrograph of FIGS. 3 and 4 of U.S. Pat. No. 5,650,222, discussed above. As shown in these figures, the cellular structure of the foam is distorted, especially when compared to the expanded HIPE foam structures shown in FIGS. 1 and 2 of the '222 patent. As can also be seen in FIGS. 3 and 4 of the '222 patent, the voids or pores (dark areas) in the collapsed foam structure have been flattened or elongated. (It is noted that the foams depicted in the '222 patent are in sheet form; as discussed below, while foams in sheet forms are useful herein, in a preferred embodiment, the foam will be in particulate form when combined with an osmotic absorbent.) The cellular structure of another HIPE-derived foam (in its expanded state) useful herein is depicted in FIGS. 3 and 4 herein. The preparation of this particular foam and related foams are described herein in Examples 2 through 4, and these very high surface area foams are described in more detail in co-pending U.S. patent application Ser. No. 09/042,429, filed Mar. 13, 1998 by T. A. DesMarais titled "HIGH SUCTION POLYMERIC FOAM MATERIALS" (P&G Care 7052) and co-pending U.S. patent application Ser. No. 09/042,418, filed Mar. 13, 1998 by T. A. DesMarais et al. titled "ABSORBENT MATERIALS FOR DISTRIBUTING AQUEOUS LIQUIDS" (P&G Case 7051), the disclosure of each of which is incorporated by reference herein.

Following compression and/or thermal drying/vacuum dewatering, the collapsed polymeric foam may reexpand when wetted with aqueous liquids. Surprisingly, these polymeric foams remain in this collapsed, or unexpanded, state for significant periods of time, e.g., up to at least about 1 year. The ability of these polymeric foams to remain in this collapsed/unexpanded state is believed to be due to capillary forces, and in particular the capillary pressures developed within the foam structure. As used herein, "capillary pressures" refers to the pressure differential across the liquid/air interface due to the curvature of meniscus within the narrow confines of the pores in the foam. [See Chatterjee, "Absorbency," *Textile Science and Technology*, Vol. 7, 1985, p. 36.]

After compression, and/or thermal drying/vacuum dewatering to a practicable extent, these polymeric foams have residual water that includes both the water of hydration associated with the hygroscopic, hydrated salt incorporated therein, as well as free water absorbed within the foam. This residual water (assisted by the hydrated salts) is believed to exert capillary pressures on the resulting collapsed foam structure. Collapsed polymeric foams of the present invention can have residual water contents of at least about 4%, typically from about 4 to about 40%, by weight of the foam when stored at ambient conditions of 72° F. (22° C.) and 50% relative humidity. Preferred collapsed polymeric foams have residual water contents of from about 5 to about 30% by weight of the foam.

A key parameter of these foams is their glass transition temperature. The Tg represents the midpoint of the transition between the glassy and rubbery states of the polymer. Foams that have a higher Tg than the temperature of use can be very strong but will also be rigid and potentially prone to fracture. Such foams also typically take a long time to recover to the expanded state when wetted with aqueous liquids colder than the Tg of the polymer after having been stored in the collapsed state for prolonged periods. The desired combination of mechanical properties, specifically strength and resilience, typically necessitates a fairly selective range of monomer types and levels to achieve these desired properties.

For foams useful in the present invention, the Tg should be as low as possible, so long as the foam has acceptable strength at in-use temperatures. Accordingly, monomers are selected as much as possible that provide corresponding homopolymers having lower Tg's. It has been found that the chain length of the alkyl group on the acrylate and methacrylate comonomers can be longer than would be predicted from the Tg of the homologous homopolymer series. Specifically, it has been found that the homologous series of alkyl acrylate or methacrylate homopolymers have a minimum Tg at a chain length of 8 carbon atoms. By contrast, the minimum Tg of the copolymers of the present invention occurs at a chain length of about 12 carbon atoms. (While the alkyl substituted styrene monomers can be used in place of the alkyl acrylates and methacrylates, their availability is currently extremely limited).

The shape of the glass transition region of the polymer can also be important, i.e., whether it is narrow or broad as a function of temperature This glass transition region shape is particularly relevant where the in-use temperature (usually ambient or body temperature) of the polymer is at or near the Tg. For example, a broader transition region can mean an incomplete transition at in-use temperatures. Typically, if the transition is incomplete at the in-use temperature, the polymer will evidence greater rigidity and will be less resilient. Conversely, if the transition is completed it the in-use temperature, then the polymer will exhibit faster recovery from compression when wetted -with aqueous liquids. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in the Test Methods section of U.S. Pat. No. 5,650,222).

(2) Vertical Hang Sorption Height

The high surface area polymeric foams useful herein can be also be described in terms of their vertical hang sorption height (hereafter "VHSH"). The VHSH height at X % is the height in cm where X % of the 0 cm capacity (or FAC) is retained in the foam. A typical value of importance is the VHSH at 90%, though in principle X may be any value. The most reproducible measure for VHSH is achieved at X=90%, within the experience of the inventors. It will be obvious to one skilled in the art that this single point value does not fully express the shape of the curve obtained in a plot of capacity vs. height. The single point however serves as a practical point of comparison for the foams useful herein. In this regard, when the foams are to be used in combination with an osmotic absorbent, the foams will typically have an equilibrium 90% VHSH of at least about 20 cm, preferably at least about 40 cm, still more preferably at least about 60 cm, still more preferably at least about 70 cm and still more preferably at least about 80 cm. Typically, preferred polymeric foams used in combination with an osmotic absorbent will have a 90% VHSH of from about 20 to about 90 cm, more typically from about 60 to about 90 cm, more typically from about 70 to about 90 cm, still more typically from about 80 to about 90 cm. With respect to foams that are used alone (i.e., no osmotic absorbent is used), the foam will have a 90% VHSH of at least about 60 cm, preferably at least about 70 cm, more preferably at least about 80 cm. Typically, when used alone, the polymeric foams will have a 90% VHSH of from about 60 to about 90 cm, more typically from about 70 to about 90 cm, still more typically from about 80 to about 90 cm.

The difference in the 90% VHSH values for foams used in these two different embodiments is due primarily to the fact that when the foam is used in combination with an osmotic absorbent, the primary benefit provided by the foam is its high surface area, which contributes to overall suction capacity of the member. That is, the foam functions primarily as a transport medium for liquid delivery to the osmotic absorbent and absorbent capacity of the foam is of secondary importance. In contrast, when the foam is used alone, it must also have significant absorbent capacity to compensate for the lack of absorbent capacity provided by the osmotic absorbent. In this regard, 90% VHSH is a measure of absorbent capacity.

The method for measuring 90% VHSH is described in detail in the Test Methods section below. As indicated, where the high surface area polymeric foam is in particulate form when combined with the osmotic absorbent, 90% VHSH is measured on the corresponding foam in sheet form (i.e., prior to forming particulates). Where the foam is formed into particles (or beads) during the polymerization process, a similar foam can be formed into sheets for assessing the foam's 90% VHSH.

(3) Capillary Suction Specific Surface Area

While the high surface area materials in general have been described in terms of their capillary sorption absorbent capacity, the high surface area polymeric foams useful herein may also be described in terms of their capillary suction specific surface area (hereafter referred to as "CSSSA"). In general, CSSSA is a measure of the test-liquid accessible surface area of the polymeric network forming a particular foam per unit mass of the bulk foam material (polymer structural material plus solid residual material). Capillary suction specific surface area is determined both by the dimensions of the cellular units in the foam and by the density of the polymer, and is thus a way of quantifying the total amount of solid surface provided by the foam network to the extent that such a surface participates in absorbency. For purposes of characterizing the foams useful herein, CSSSA is measured on a sheet of the foam in question, even where the foam is in particle form when incorporated in a storage absorbent member.

The CSSSA of a foam is particularly relevant to whether the foam will provide the requisite capillary suction for use in preparing storage absorbent members of the present invention. This is because the capillary pressure developed within the foam structure is proportional to the capillary suction specific surface area. In addition, the CSSSA is relevant to whether adequate capillary pressures are developed within the foam structure to keep it in a collapsed state until wetted with aqueous liquids. Assuming other factors such as the foam density and adhesion tension are constant, this means that, as the CSSSA is increased (or decreased), the capillary pressure within the foam structure also increases (or decreases) proportionately.

For purposes of the present invention, CSSSA is determined by measuring the amount of capillary uptake of a low surface tension liquid (e.g., ethanol) which occurs within a foam sample of a known mass and dimensions. A detailed description of such a procedure for determining foam specific surface area is :;et forth in the Test Methods section of U.S. Pat. No. 5,387,207, which is incorporated by reference.

The collapsed polymeric foams of the present invention useful as absorbents are those that have a CSSSA of at least about 3 $m^2/g$. Typically, the CSSSA is in the range from about 3 to about 30 $m^2/g$, preferably from about 4 to about 17 $m^2/g$, most preferably from about 5 to about 15 $m^2/g$. Foams having such CSSSA values (with expanded state densities of from about 0.010 to about 0.033 g/cc) will generally possess an especially desirable balance of absorbent capacity, liquid-retaining and liquid-wicking or distribution characteristics for aqueous liquids such as urine. In addition, foams having such CSSSA can develop a sufficient capillary pressure to keep the foam in a collapsed, unexpanded state until wetted with such aqueous liquids.

(4) Capillary Pressures and Forces Within Foam Structure

As discussed above, for particularly preferred collapsable polymeric foams, in their collapsed state the capillary pressures developed within the foam structure at least equal the forces exerted by the elastic recovery or modulus of the compressed polymer. In other words, the capillary pressure necessary to keep the Collapsed foam relatively thin is determined by the countervailing force exerted by the compressed polymeric foam as it tries to "spring back." The elastic recovery tendency of polymeric foams can be estimated from stress-strain experiments where the expanded foam is compressed to about ⅙ (17%) of its original, expanded thickness and then held in this compressed state until a relaxed stress value is measured. Alternatively, and for the purposes of the present invention, the relaxed stress value is estimated from measurements on the polymeric foam in its collapsed state when in contact with aqueous liquids, e.g., water. This alternative relaxed stress value is hereafter referred to as the "expansion pressure" of the foam. The expansion pressure for collapsed polymeric foams of the present invention is about 50 kiloPascals (kPa) or less and typically from about 7 to about 40 kPa. A detailed description of a procedure for estimating the expansion pressure of foams is set forth in the Test Methods section of U.S. Pat. No. 5,387,207.

(5) Free Absorbent Capacity

Another relevant property of the high surface area polymeric foams useful in the present invention is their free absorbent capacity. "Free absorbent capacity" (or "FAC") is the total amount of test liquid (synthetic urine) which a given foam sample will absorb into its cellular structure per unit mass of solid material in the sample. To be especially useful in the storage absorbent members of the present invention, the polymeric foams should have a free absorbent capacity of from about 30 to about 100 mL, preferably from about 30 to about 75 mL of synthetic urine per gram of dry foam material. The procedure for determining the free absorbent capacity of the foam is described hereafter in the Test Methods section of U.S. Pat. No. 5,650,222.

(6) Expansion Factor

Upon exposure to aqueous liquids, preferred collapsed polymeric foams absorb the liquids and expand. The polymeric foams, in their expanded state, absorb more liquid than most other foams. The "expansion factor" for these foams is at least about 4×, i.e. the thickness of the foam in its expanded state is at least about 4 times the thickness of the foam in its collapsed state. The collapsed foams preferably have an expansion factor in the range of from about 4× to about 15×, more preferably from about 5× to about 10×.

For the purposes of the present invention, the relationship between expanded and collapsed thickness for compressively dewatered foams can be empirically predicted from the following equation:

$$\text{thickness}_{expanded} = \text{thickness}_{collapsed} \times ((0.133 \times W{:}O \text{ ratio}) \pm 2)$$

where:

$\text{thickness}_{expanded}$ is the thickness of the foam in its expanded state;

$\text{thickness}_{collapsed}$ is the thickness of the foam in its collapsed state;

and W:O ratio is the water-to-oil ratio of the HIPE from which the foam is made.

Thus, a typical polymeric foam made from an emulsion with a water-to-oil ratio of 60:1 would have a predicted expansion factor of 8.0, i.e., an expanded thickness 8 times the collapsed thickness of the foam. The procedure for measuring the expansion factor is described hereafter in the Test Methods section of U.S. Pat. No. 5,650,222.

(7) Resistance to Compression Deflection

A relevant mechanical feature of the high surface area polymeric foams useful in the present invention is their strength in their expanded state, as determined by resistance to compression deflection (RTCD). The RTCD exhibited by the foams herein is a unction of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as the high surface area portion of The absorbent members of the present invention, the polymeric foams should be suitably resistant to deformation or compression by forces encountered in use. Foams which do not possess sufficient foam strength in terms of RTCD may provide the requisite capillary suction capacity under no-load conditions but will not provide those capacities under the compressive stress caused by the motion and activity of the user of the absorbent articles that contain the foam.

The RTCD exhibited by the polymeric foams useful in the present invention can be quantified by determining the amount of strain produced in a sample of saturated foam held under a certain confining pressure for a specified temperature and period of time. The method for carrying out this particular type of test is described hereafter in the Test Methods section of U.S. Pat. No. 5,650,222. Foams useful herein will preferably exhibit a RTCD such that a confining pressure of 5.1 kPa produces a strain of typically about 90% or less compression of the foam structure when it has been saturated to its free absorbent capacity with synthetic urine having a surface tension of 65±5 dynes/cm. Preferably the strain produced under such conditions will be in the range from about 1 to about 90%, more preferably from about 1 to about 25%, still more preferably from about 2 to about 10%, still more preferably from about 2 to about 5%.

(8) Other Properties of Polymeric Foam

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

A number of techniques are available for determining the average cell size of foams. The most useful technique, however, for determining cell size in foams involves a simple measurement based on the scanning electron photomicrograph of a foam sample.

The cell size measurements given herein are based on the number average cell size of the foam in its expanded state, e.g., as shown in FIG. 1 of U.S. Pat. No. 5,650,222. The foams useful in accordance with the present invention will preferably have a number average cell size of about 80 $\mu$M or less, and typically from about 5 to about 50 $\mu$m.

"Foam density" (i.e., in grams of foam per cubic centimeter of foam volume in air) is specified herein on a dry basis. The amount of absorbed water-soluble residual materials, e.g., residual salts and liquid left in the form, for example, after HIPE polymerization, washing and/or hydrophilization, is disregarded in calculating and expressing foam density. Foam density does include, however, other water-insoluble residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure described more fully in the Test Methods section of U.S. Pat. No. 5,387,207 (Dyer et al.) issued Feb. 7, 1995, supra, is one method that can be employed for density determination. In their collapsed state, polymeric foams useful in the present invention have dry basis density values (exclusive of any residual salts and or water) in the range of from about 0.1 to about 0.2 g/cc, preferably from about 0.11 to about 0.19 g/cc, and most preferably from about 0.12 to about 0.17 g/cc. In their expanded state, polymeric foams useful herein will have dry basis density values in the range of from about 0.01 to about 0.033 g/cc, preferably from about 0.013 to about 0.033 g/cc.

Vertical wicking, i.e., liquid wicking in a direction opposite from gravitational force, is a desirable performance attribute for polymeric foams useful herein. For the purposes of this invention, vertical wicking rate is reflective of the permeability of the material, and thus, the ability of the material to deliver liquid to the hydrogel-forming absorbent polymer or other osmotic absorbent.

Vertical wicking rate is determined by measuring the time taken for a colored test liquid (e.g., synthetic urine) in a reservoir to wick a vertical distance of 5 cm through a test strip of foam of specified size. The vertical wicking procedure is described in greater detail in the Test Methods section of U.S. Pat. No. 5,387,207, but is performed at 31° C., instead of 37° C. To be especially useful in absorbent members for absorbing urine, the foams useful herein will preferably wick synthetic urines (65±5 dynes/cm) to a height of 5 cm in no more than about 15 minutes. More preferably, the preferred foam absorbents of the present invention wick synthetic urine to a height of 5 cm in no more than about 10 minutes.

The vertical wicking absorbent capacity test measures the amount of test liquid per gram of absorbent foam that is held within each one in. (2.54 cm) vertical section of the same standard size foam sample used in the vertical wicking test. Such a determination is generally made after the sample has been allowed to vertically wick test liquid to equilibrium (e.g., after about 18 hours). Like the vertical wicking test, the vertical wicking absorbent capacity test is described in greater detail in the Test Methods section of U.S. Pat. No. 5,387,207 (Dyer et al.) issued Feb. 7, 1995, supra. High vertical wicking absorbent capacities at high heights are theoretically equivalent to high capillary sorption absorbent capacities at high heights. Since the sheet form of the foams useful herein is amenable to the former test and the former test is more easily and cheaply performed, the data from the former test are recommended as the means of characterizing this important parameter of the foams of this invention.

While high capillary suction foams may be in sheet form when combined with osmotic absorbent (e.g., hydrogel-forming absorbent polymer), in a particularly preferred embodiment, the polymeric foam will be in particle form and will be mixed with particles of hydrogel-forming polymer to provide a blend. That is, while the foam may initially be prepared in sheet form, these sheets may be processed to provide particles of foam which are then combined with the hydrogelling polymer. As discussed above, the foams useful herein, and processes for their preparation, are described in great detail in U.S. Pat. No. 5,387,207, U.S. Pat. No. 5,650,222, co-pending U.S. patent application Ser. No. 09/042,429, filed Mar. 13, 1998 by T. A. DesMarais titled "HIGH SUCTION POLYMERIC FOAM MATERIALS" (P&G Case 7052) and cc-pending U.S. patent application Ser. No. 09/042,418, filed Mar. 13, 998 by T. A. DesMarais et al. titled "ABSORBENT MATERIALS FOR DISTRIBUTING AQUEOUS LIQUIDS" (P&G Case 7051). Foam particles may be prepared by first forming a sheet of foam per the teachings of these references, followed by mechanical processing the foam to provide particles (e.g., pulverizing, cutting, chopping, etc.) of the desired dimension. Alternatively, foam particles may be prepared directly from emulsion in the form of polymeric microbeads, as described in U.S. Pat. No. 5,653,922, issued Aug. 5, 1997 to Li et al., and U.S. Pat. No. 5,583,162, issued Dec. 10, 1996 to Li et al., the disclosure of each of which is incorporated by reference herein. Specific embodiments for making polymer foam/hydrogel-forming polymer blends are discussed in more detail below.

Applicants have also found that the high surface area foams, when used as a transport medium for fluid delivery to an osmotic absorbent, may optionally comprise a fluid so as to provide increased transfer of urine or other body fluids to the osmotic absorbent of the storage absorbent member. The pre-wetting fluid partially fills the polymeric foam and, without wishing to be held to a particular theory, increases the uptake rate of the foam. Ideally, polymeric foam comprising pre-wetting fluid(s) should be shelf stable, with sufficiently low water activity to prevent microbial growth and prevent evaporative water loss and not migrate out of the foam over time. Water can be used as a pre-wetting fluid to provide the absorption performance but may not by itself meet the other requirements.

B. Storage Absorbent Members Comprising Osmotic Absorbent and High Surface Area Materials As indicated above, in one embodiment, the storage absorbent members of the present invention will comprise an osmotic absorbent, for example a hydrogel-forming absorbent polymer, and a high surface area material that facilitates transport of body fluids to the osmotic absorbent. In one such embodiment, the high surface area material will be in the form of a high surface area hydrophilic polymeric foam discussed above. Other representative materials useful in preparing the storage absorbent members of the present invention are high surface area fibers, which are described in detail below. While other osmotic absorbents may be used in the storage members, hydrogel-forming absorbent polymers are preferred. As such, these materials are described in detail.

1. Hydrogel-Forming Absorbent Polymers a. Chemical Composition

In one preferred embodiment, the storage absorbent members of the present invention will comprise at least one hydrogel-forming absorbent polymer (also referred to as hydrogel-forming polymer). Hydrogel-forming polymers useful in the present invention include a variety of water-insoluble, but water-swellable polymers capable of absorbing large quantities of liquids. Such hydrogel-forming polymers are well known in the art and any of these materials are useful in the high capillary suction absorbent members of the present invention.

Hydrogel-forming absorbent polymers materials are also commonly referred to as "hydrocolloids," or "superabsorbent" materials and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and tie respective quaternary salts thereof. Typically, hydrogel-forming absorbent polymers useful in the present invention have a multiplicity of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids aid acid anhydrides, olefinically unsaturated sulfonic acids, and mixtures thereof. As indicated above, the nature of the hydrogel-forming absorbent polymer is not critical to the members of the present invention. Nonetheless, the selection of the optimal polymeric material may enhance the performance characteristics of the present members. The disclosure that follows describes preferred properties of the absorbent polymers useful herein. These properties should not be interpreted as limitations; rather, they merely indicate the progression that has occurred in the absorbent polymer art over the past several years.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making the hydrogel-forming absorbent polymers are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the hydrogel-forming absorbent polymers. Processes for network crosslinking these polymers and typical network crosslinking agents are described in greater detail in U.S. Pat. No. 4,076,663.

While the hydrogel-forming absorbent polymer is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention.

The hydrogel-forming polymer component may a so be in the form of a mixed-bed ion-exchange composition comprising a cation-exchange hydrogel-forming absorbent polymer and an anion-exchange hydrogel-forming absorbent polymer. Such mixed-bed ion-exchange compositions are described in, e.g., U.S. patent application Ser. No. 09/003,565, filed Jan. 7, 1998 by Hird, et al. (P&G Case 6975—titled "ABSORBENT POLYMER COMPOSITIONS HAVING HIGH SORPTION CAPACITIES UNDER AN APPLIED PRESSURE"); U.S. patent application Ser. No. 09/003,905, filed Jan. 7, 1998 by Ashraf, et al. (P&G Case 6976—titled "ABSORBENT POLYMER COMPOSITIONS WITH HIGH SORPTION CAPACITY AND HIGH FLUID PERMEABILITY UNDER AN APPLIED PRESSURE"); and U.S. patent application Ser. No. 09/00,918, filed Jan. 7, 1998 by Ashraf, et al. (P&G Case 6977—titled "ABSORBENT POLYMER COMPOSITIONS HAVING HIGH SORPTION CAPACITIES UNDER AN APPLIED PRESSURE AND IMPROVED INTEGRITY IN THE SWOLLEN STATE"); the disclosure of each of which is incorporated herein by reference.

The hydrogel-forming absorbent polymers useful in the present invention can have a size, shape and/or morphology varying over a wide range. These polymers can be in the form of particles that do not have a large ratio of greatest dimension to smallest dimension (e.g., granules, pulverulents, interparticle aggregates, interparticle crosslinked aggregates, and the like) and can be in the form of fibers, sheets, films, foams, flakes and the like. The hydrogel-forming absorbent polymers can also comprise mixtures with low levels of one or more additives, such as for example powdered silica, surfactants, glue, binders, and the like. The components in this mixture can be physically and/or chemically associated in a form such that the hydrogel-forming polymer component and the non-hydrogel-forming polymer additive are not readily physically separable.

The hydrogel-forming absorbent polymers can be essentially non-porous (i.e., no internal porosity) or have substantial internal porosity.

For particles as described above, particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S. Series Alternate Sieve Designation) is considered to have a particle size between 500 and 710 μm; and a particle that passes through a sieve with 500 micron openings is considered to have a size less than 500 μm. The mass median particle size of a given sample of hydrogel-forming absorbent polymer particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the hydrogel-forming absorbent polymer particles are further described in U.S. Pat. No. 5,061,259 (Goldman et al.), issued Oct. 29, 1991, which is incorporated by reference.

For particles of hydrogel-forming absorbent polymers useful in the present invention, the particles will generally range in size from about 1 to about 2000 μm, more preferably from about 20 to about 1000 μm. The mass median particle size will generally be from about 20 to about 1500 μm, more preferably from about 50 Mm to about 1000 μm, and even more preferably from about 100 to about 800 μm.

Where relatively high concentrations (e.g. 40–60% or greater, by weight) of hydrogel forming absorbent polymer are utilized in the absorbent members of the present invention, still other properties of the absorbent polymer may be relevant. In such embodiments, the materials may have one or more of the properties described by U.S. Pat. No. 5,562,646, issued Oct. 8, 1996 to Goldman et al. and U.S. Pat. No. 5,599,335, issued Feb. 4, 1997 to Goldman et al., the disclosure of each of which is incorporated by reference herein.

b. Methods for Making

The basic hydrogel-forming absorbent polymer can be formed in any conventional manner. Typical and preferred processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987. and U.S. Pat. No. 4,625,001 (Tsubakimoto et al.), issued Nov. 25, 1986, all of which are incorporated by reference.

Preferred methods for forming the basic hydrogel-forming absorbent polymer are those involving aqueous solution or other solution polymerization methods. As described in the above-referenced U.S. Pat. Reissue No. 32,649, aqueous solution polymerization involves the use of an aqueous reaction mixture to carry out polymerization. The aqueous reaction mixture is then subjected to polymerization conditions which are sufficient to produce in the mixture, substantially water-insoluble, slightly network crosslinked polymer. The mass of polymer formed can then be pulverized or chopped to form individual particles.

More specifically, the aqueous solution polymerization method for producing the hydrogel-forming absorbent polymer comprises the preparation of an aqueous reaction mixture in which to carry out the polymerization. One element of such a reaction mixture is the acid group-containing monomer that will form the "backbone" of the hydrogel-forming absorbent polymer to be produced. The reaction mixture will generally comprise about 100 parts by weight of the monomer. Another component of the aqueous reaction mixture comprises a network crosslinking agent. Network crosslinking agents useful in forming the hydrogel-forming absorbent polymer according to the present invention are described in more detail in the above-referenced U.S. Reissue Pat. No. 32,649, U.S. Pat. No. 4,666,983, and U.S. Pat. No. 4,625,001. The network crosslinking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer). An optional component of the aqueous reaction mixture comprises a free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomers, including esters of the essential unsaturated acidic functional group-containing monomers or other co-monomers containing no carboxylic or sulfonic acid functionalities at all.

The aqueous reaction mixture is subjected to polymerization conditions which are sufficient to produce in the mixture substantially water-insoluble, but water-swellable, hydrogel-forming absorbent slightly network crosslinked polymers. The polymerization conditions are also discussed in more detail in the three above-referenced patents. Such polymerization conditions generally involve heating (thermal activation techniques) to a polymerization temperature from about 0° to about 100° C., more preferably from about 50 to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques.

The acid functional groups of the hydrogel-forming absorbent polymer formed in the aqueous reaction mixture are also preferably neutralized. Neutralization can be carried out in any conventional manner that results in at least about 25 mole percent, and more preferably at least about 50 mole percent, of the total monomer utilized to form the polymer being acid group-containing monomers that are neutralized with a salt-forming cation. Such salt-forming cations include, for example, alkali metals, ammonium, substituted ammonium and amines as discussed in further detail in the above-references U.S. Reissue Pat. No. 32,649.

While it is preferred that the particulate versions of hydrogel-forming absorbent polymer be manufactured using an aqueous solution polymerization process, it is also possible to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as described before is suspended in the form of tiny droplets in a matrix of a water-immiscible, inert organic solvent such as cyclohexane. The resultant particles of hydrogel-forming absorbent polymer are generally spherical in shape. Inverse suspension polymerization procedures are described in greater detail in U.S. Pat. No. 4,340,706 (Obaysashi et al.), issued Jul. 20, 1982, U.S. Pat. No. 4,506,052 (Flesher et al.), issued Mar. 19, 1985, and U.S. Pat. No. 4,735,987 (Morita et al.), issued Apr. 5, 1988, all of which are incorporated by reference.

Surface crosslinking of the initially formed polymers is a preferred process for obtaining hydrogel-forming absorbent polymers having relatively high porosity hydrogel-layer ("PHL"), performance under pressure ("PUP") capacity and saline flow conductivity ("SFC") values, which may be beneficial in the context of the present invention. Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308

(Makita), issued May 6, 1986; U.S. Pat. No. 4,734,478 Tsubakimoto), issued Mar. 29, 1988; U.S. Pat. No. 5,164,459 (Kimura et al.), issued Nov. 17, 1992; published German patent application 4,020,780 (Dahmen), published Aug. 29, 1991; and published European patent application 509,708 (Gartner), published Oct. 21, 1992; all of which are incorporated by reference. See also, U.S. Pat. No. 5,562,646 (Goldman et al.), issued Oct. 8, 1996 and U.S. Pat. No. 5,599,335 (Goldman et al.), issued Feb. 4, 1997.

The hydrogel-forming absorbent polymer particles prepared according to the present invention are typically substantially dry. The term "substantially dry" is used herein to mean that the particles have a liquid content, typically water or other solution content, less than about 50%, preferably less than about 20%, more preferably less than about 10%, by weight of the particles. In general, the liquid content of the hydrogel-forming absorbent polymer particles is in the range of from about 0.01% to about 5% by weight of the particles. The individual particles can be dried by any conventional method such as by heating. Alternatively, when the particles are formed using an aqueous reaction mixture, water can be removed from the reaction mixture by azeotropic distillation. The polymer-containing aqueous reaction mixture can also be treated with a dewatering solvent such as methanol. Combinations of these drying procedures can also be used. The dewatered mass of polymer can then be chopped or pulverized to form substantially dry particles of the hydrogel-forming absorbent polymer.

2. High Surface Area Materials

With respect to storage absorbent members of the present invention which comprise an osmotic absorbent (for example, hydrogel-forming absorbent polymers), the member will also comprise a high surface area material. It is this high surface area material that provides, either itself or in combination with the hydrogel-forming absorbent polymer, the members with high capillary sorption absorbent capacity. As discussed herein, high surface area materials are described, at least in one regard, in terms of their capillary sorption absorbent capacity (measured without hydrogel-forming polymer or any other optional material contained in the actual storage absorbent member, such as adhesives, bonding agents, etc.). It is recognized that materials having high surface areas may have uptake capacities at very high suction heights (e.g., 100 cm or higher). This allows the high surface area materials to provide one or both of the following functions: i) a capillary pathway of liquid to the osmotic absorbents, and/or ii) additional absorbent capacity. Thus, while the high surface area materials may be described in terms of their surface area per weight or volume, Applicants herein alternatively use capillary sorption absorbent capacity to describe the high surface area material because capillary sorption absorbent capacity is a performance parameter that generally will provide the absorbent members of the present invention with the requisite suction capabilities to provide improved absorbent articles. It will be recognized that certain high surface area materials, e.g. glass microfibers, will themselves not exhibit particularly high capillary sorption absorbent capacity at all heights, especially very high heights (e.g., 100 cm and higher). Nonetheless, such materials may provide the desired capillary pathway of liquid to the hydrogel-forming absorbent polymer or other osmotic absorbent to provide the requisite capillary sorption absorbent capacities, even at relatively high heights, when combined with the hydrogel-forming polymer or other osmotic absorbents.

Any material having sufficient capillary sorption absorbent capacity when used in combination with the hydrogel-forming absorbent polymer or other osmotic absorbent will be useful in the storage absorbent members of the present invention. In this regard, the term "high surface area material" refers to any material that itself (i.e., as measured without the osmotic absorbent or any other optional material that makes up the storage absorbent member) exhibits one or more of the following capillary sorption absorbent capacities: (I) A capillary sorption absorbent capacity at a height of 35 cm of at least about 5 g/g, preferably at least about 8 g/g, more preferably at least about 12 g/g, (II) A capillary sorption absorbent capacity at a height of 70 cm of at least about 3 g/g, preferably at least about 5 g/g, more preferably at least about 7 g/g, (III) A capillary sorption absorbent capacity at a height of 120 cm of at least about 2 g/g, preferably at least about 3 g/g, more preferably at least about 4 g/g, still more preferably at least about 5 g/g; or (IV) A capillary sorption absorbent capacity at a height of 200 cm of at least about 1 g/g, preferably at least about 2 g/g, more preferably, at least about 3 g/g, still more preferably at least about 5 g/g.

In one embodiment, the high surface area material will be fibrous (hereafter referred to as "high surface area fibers") in character, so as to provide a fibrous web or fibrous matrix when combined with the hydrogel-forming absorbent polymer or other osmotic absorbent. These materials are described in detail below. Alternatively, and in a particularly preferred embodiment, the high surface area material will be an open-celled, hydrophilic polymeric foam (hereafter referred to as "high surface area polymeric foams" or more generally as "polymeric foams"). These materials are described in detail above.

High surface area fibers useful in the present invention include those that are naturally occurring (modified or unmodified), as well as synthetically made fibers. The high surface area fibers have surface areas much greater than fibers typically used in absorbent articles, such as wood pulp fibers. The high surface area fibers used in the present invention will desirably be hydrophilic. As used herein, the term "hydrophilic" describes fibers, or surfaces of fibers, that are wettable by aqueous liquids (e.g., aqueous body liquids) deposited on these fibers. Hydrophilicity and wettability are typically defined in terms of contact angle and the surface tension of the liquids and solids involved. This is discussed in detail in the American Chemical Society publication entitled Contact Angle, Wettability and Adhesion, edited b)y Robert F. Gould (Copyright 1964). A fiber, or surface of a fiber, is said to be wetted by a liquid (i.e., hydrophilic) when either the contact angle between the liquid and the fiber, or its surface, is less than 90°, or when the liquid tends to spread spontaneously across the surface of the fiber, both conditions normally co-existing. Conversely, a fiber or surface is considered to be hydrophobic if the contact angle is greater than 90° and the liquid does not spread spontaneously across the surface of the fiber. The hydrophilic character of the fibers useful herein may be inherent in the fibers, or the fibers may be naturally hydrophobic fibers that are treated to render them hydrophilic. Materials and methods for providing hydrophilic character to naturally hydrophobic fibers are well known.

High surface area fibers useful herein will have capillary suction specific surface areas in the same range as the polymeric foams described above. Typically, however, high surface area fibers are characterized in terms of BET surface area High surface area fibers useful herein include glass microfibers such as, for example, glass wool available from Evanite Fiber Corp. (Corvallis, Oreg.). Glass microfibers useful herein will typically have fiber diameters of not more than about 0.8 µm, more typically from about 0.1 µm to about 0.7 µm. These microfibers will have surface areas of at least about 2 m²/g, preferably at least about 3 m²/g. Typically, the surface area of glass microfibers will be from about 2 m²/g to about 15 m²/g. Representative glass microfibers for use herein are those available from Evanite Fiber Corp. as type 104 glass fibers, which have a nominal fiber diameter of about 0.5 µm. These glass microfibers have a calculated surface area of about 3.1 m²/g.

Another type of high surface area fibers useful herein are fibrillated cellulose acetate fibers. These fibers (referred to herein as "fibrets") have high surface areas relative to cellulose-derived fibers commonly employed in the absorbent article art. Such fibrets have regions of very small diameters, such that their particle size width is typically from about 0.5 to about 5 µm. These fibrets typically have surface area of about 20 m²/g. Representative fibrets useful as the high surface area materials herein are available from Hoechst Celanese Corp. (Charlotte, N.C.) as cellulose acetate Fibrets®. For a detailed discussion of fibrets, including their physical properties and methods for their preparation, see "Cellulose Acetate Fibrets: A Fibrillated Pulp With High Surface Area", Smith, J. E., *Tappi Journal*, Dec. 1988, p. 237; and U.S. Pat. No. 5,486,410 (Groeger et al.) issued Jan. 23, 1996; the disclosure of each of which is incorporated by reference herein.

In addition to these fibers, the skilled artisan will recognize that other fibers well known in the absorbency art may be modified to provide high surface area fibers for use herein. Representative fibers that may be modified to achieve high surface areas required by the present invention are disclosed in U.S. Pat. No. 5,599,335, supra (see especially columns 21–24).

Regardless of the nature of the high surface area fibers utilized, the fibers and the osmotic absorbent will be discrete materials prior to combination. As used herein, the term "discrete" means that the high surface area fibers and the osmotic absorbents are each formed prior to being combined to form the storage absorbent member. In other words, the high surface area fibers are not formed subsequent to mixing with the osmotic absorbent (e.g., hydrogel-forming absorbent polymer), nor is the osmotic absorbent formed after combination with the high surface area fibers. Combining of the discrete respective components ensures that the high surface area fibers will have the desired morphology and, more importantly, the desired surface area.

C. Optional Components and Materials

Storage absorbent members according to the present invention can include other optional components that can be present in absorbent webs. For example, a reinforcing scrim can be positioned within the storage absorbent member, or between the respective absorbent members of the absorbent core. Such reinforcing scrims should be of such configuration as to not form interfacial barriers to liquid transfer, especially if positioned between the respective absorbent members of the absorbent core. In addition, several binders may be used to provide dry and wet integrity to the absorbent core and/or the absorbent storage member itself. In particular, hydrophilic glue fibers may be used to provide bonds between the high surface area material; and the osmotic absorbent material. This is in particular critical for particulate high surface area materials. It is preferred that the amount of binder used is as low as possible, so as not to impair the capillary sorption properties of the absorbent member. However, the skilled artisan will recognize that there are also binders that may enhance the capillary sorption properties of the absorbent member such as fiberized hydrophilic glue with sufficiently high surface area. In this case, the high surface area hydrophilic glue may provide both the liquid handling function and the integrity function, in one material. Also, the respective absorbent member, or the entire absorbent core, can be enveloped within a liquid pervious sheet, such as a tissue paper sheet, to obviate user concern regarding loose particulate absorbent polymer, as long as the capillary continuity is not disturbed.

Other optional components that can be included are materials to control odor, contain fecal matter, etc. Also, any absorbent member comprising particulate osmotic absorbent or high surface area material, or the entire absorbent core, can be enveloped within a liquid pervious sheet, such as a tissue paper sheet, to obviate user concern regarding loose particulate absorbent polymer.

IV. Other Storage Absorbent Member Materials and Properties

The high capillary suction absorbent capacity storage absorbent members of the present invention function as liquid storage members in the absorbent core. The principle function of such liquid storage members is to absorb the discharged body liquid either directly or from other absorbent members (e.g., liquid acquisition/distribution members), and then retain such liquid, even when subjected to pressures normally encountered as a result of the wearer's movements. It should be understood, however, that such absorbent members can serve functions other than liquid storage.

In those embodiments where an osmotic absorbent is used, the amount of hydrogel-forming absorbent polymer or other osmotic absorbent contained in the storage absorbent member may vary significantly. Furthermore, the concentration of osmotic absorbent may vary throughout a given member. In other words, a member may have regions of relatively higher and relatively lower osmotic absorbent concentrations. Without wishing to be bound by theory, it is believed that the minimum amount of high surface area material mixed with the hydrogel-forming polymer or other osmotic absorbent material must be sufficient so as to fill the interstitial spaces between hydrogel-forming absorbent polymer particles or other osmotic absorbent to a significant degree in the dry and wet state, so as to provide capillary continuity and sufficient liquid flow to the hydrogel-forming absorbent polymer.

In those preferred embodiments where the osmotic absorbent is in the form of a hydrogel-forming absorbent polymer, in measuring the concentration in a given region of an absorbent member, the percent by weight of the hydrogel-forming absorbent polymer relative to the combined weight of hydrogel-forming absorbent polymer and any other components (e.g., fibers, polymeric foams, etc.) that are present in the region containing the hydrogel-forming polymer is used. With this in mind, the concentration of the hydrogel-forming absorbent polymers in a given region of an absorbent member of the present invention can be at least about 50%, at least about 60%, at least about 70%, at least about 80%, or at least about 90%, by total weight of the absorbent member. (Similar ranges will apply where another osmotic absorbent is employed.)

Notwithstanding the fact that regions of an storage absorbent member may comprise relatively high concentrations of hydrogel-forming absorbent polymer or other osmotic absorbent, where the high surface area material is fibrous in nature, the member will comprise, on an aggregate basis (i.e., total weight of high surface area fibers used in member divided by the total weight of the absorbent member×100%), at least about 25% by weight, of the high surface area fibers.

A lower limit of about 25% fibers is believed necessary to impart the necessary requisite capillary suction to the absorbent member. Preferably the storage absorbent members will comprise at least about 30%, by weight, more preferably at least about 35%, by weight, of the high surface area fibers. Typically, an absorbent member of the present invention will comprise, on an aggregate basis, from about 25 to about 90%, by weight, more typically from about 30 to about 85%, by weight, still more typically from about 35 to about 80%, by weight, high surface area fibers.

In those embodiments where the high surface area material used with the osmotic absorbent is a polymeric foam, the absorbent members will preferably comprise at least about 1%, by weight (on an aggregate basis), polymeric foam. The ability to use very low levels of polymeric foam, relative to the amount of high surface area fibers discussed above, is due to various factors, including the very low density of these foams, the fact that the foams are open-celled, that the foams themselves contribute to overall absorbent capacity, and the like. The storage absorbent member will preferably comprise at least about 10%, by weight, more preferably at least about 15%, by weight, still more preferably at least about 20%, by weight, polymeric foam. Typically, such storage absorbent members will comprise from about 1 to about 93%, by weight, more typically from about 10 to about 90%, by weight, still more typically from about 15 to about 85%, by weight, and still more typically from about 20 to about 80%, by weight, of the polymeric foam material. As discussed above, these weight % ranges are based on the aggregate weights of the respective materials in the storage absorbent member, it is recognized that regions of the storage absorbent member may contain greater and lesser amounts of the materials. Of course, the relative levels of the osmotic absorbent (e.g., hydrogel-forming absorbent polymer) and high surface area material will be dictated by, for example, the absorptive capacity of the osmotic absorbent, the specific high surface area material used, the nature of the high surface area material (e.g., sheet or particle foam, particle size), etc. In this regard, although high levels of osmotic absorbent provide absorbent members for making thin absorbent articles, to achieve the requisite level of capillary suction discussed above, there must be sufficient high surface area material to provide such suction capacity. Without wishing to be bound by theory, it is believed that three primary properties of the preferred collapsible polymeric foam materials described above allow these foams to function particularly effectively in high suction storage absorbent members. These three properties are: (i) relatively low density, (ii) the ability to readily distribute liquid within itself, and (iii) the ability to remain collapsed but then expand, upon absorption of sufficient liquid, along with the preferred hydrogel-forming absorbent polymers as they swell upon imbibation of liquid. This latter property maintains contact between the foam material and the hydrogel-forming particles as the member absorbs fluid.

Figure 5:
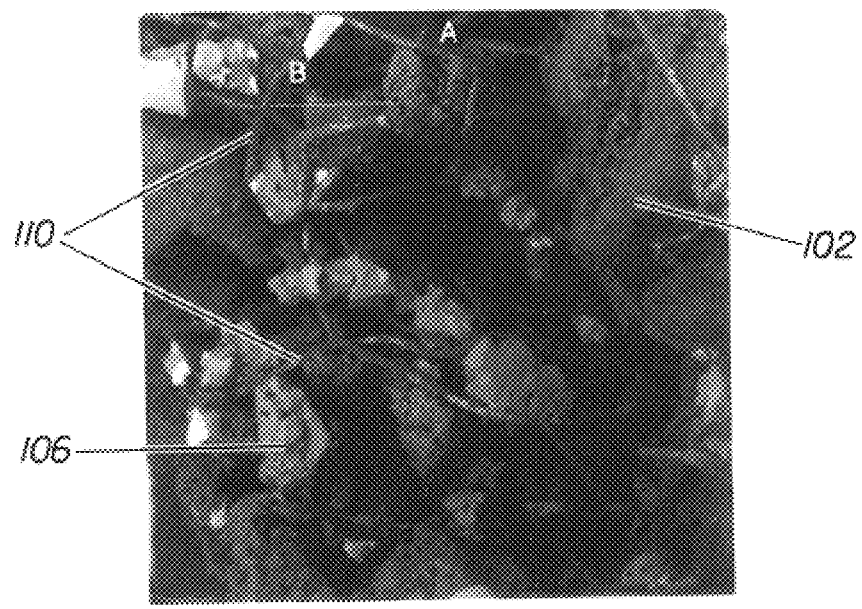
FIG. 5 is a photomicrograph of a storage absorbent member of the present invention, comprising particulate hydrogel-forming absorbent polymer and particulate polymeric absorbent foam.
Figure 6:
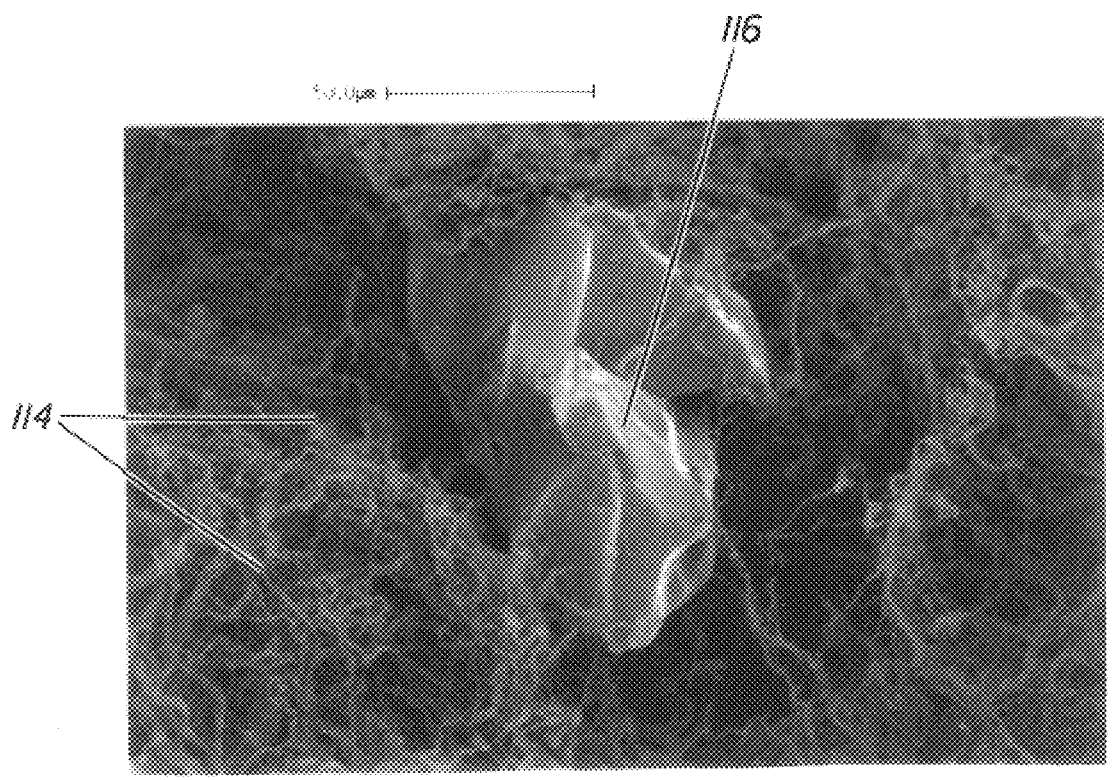
FIG. 6 is a photomicrograph of a storage absorbent member of the present invention, comprising particulate hydrogel-forming absorbent polymer and high surface area cellulose acetate fibrets.
Figure 7:
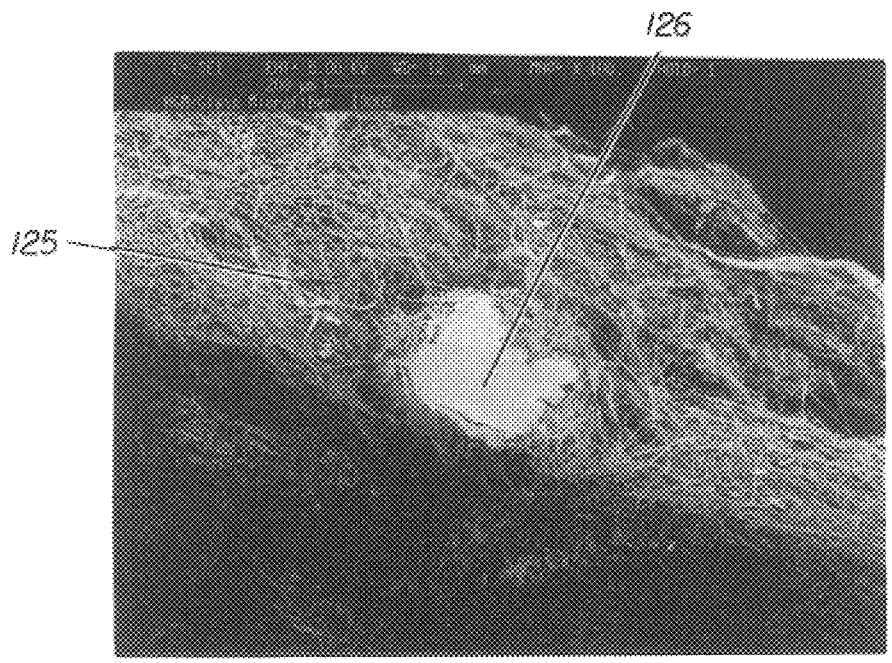
FIG. 7 is a photomicrograph of a storage absorbent member of the present invention, comprising particulate hydrogel-forming absorbent polymer and high surface area glass microfibers.

Representative storage absorbent members of the present invention are shown via photomicrograph in FIGS. 3, 4, 5, 6 and 7. FIGS. 3 and 4 depict high suction polymeric foams which may alone (preferably in sheet form) function as the storage absorbent member. FIGS. 5, 6, and 7 depict storage absorbent members comprising an osmotic absorbent (specifically a hydrogel-forming absorbent polymer) and a high surface area material. Referring to FIG. 5, a mixture of particulate hydrophilic, polymeric foam materials, shown as 102, and particulate hydrogel-forming absorbent polymer, shown as 106, are in contact with one another. Also shown are glue filaments, designated as 110, which provide integrity to the structure and maintain contact of foam particles 102 and hydrogel-forming polymer particles 106. Referring to FIG. 6, a single particle of hydrogel-forming polymer 116 is surrounded by numerous fibrets, which are shown generally as 114. Finally, in FIG. 7, a cross section of a single hydrogel-forming particle 126 is surrounded by a plurality of glass fibers, shown generally as 125.

With respect to storage absorbent members comprising a hydrogel-forming absorbent polymer, in addition to the high surface area material and the hydrogel-forming absorbent polymer, the storage absorbent members of the present invention may comprise other optional materials. For example, to provide integrity of the mixture of the required materials, the storage absorbent members may comprise an adhesive or binder material. Such materials may be particularly desired where the high surface area material is particulate in nature.

When integrity is introduced via a binder material, suitable binders are melt-blown adhesives such as those described in U.S. Pat. No. 5,560,878, issued Oct. 1, 1996 to Dragoo et al., the disclosure of which is incorporated herein by reference. Processes for combining melt-blown adhesives with the requisite hydrogel-forming polymer and high surface area material is also described in detail in the '878 patent.

As another example of a material that will provide integrity of the mixture, in absorbent members comprising a blend of hydrogel-forming polymer and high surface area fibers and/or particulate polymeric foam, the member can comprise a thermoplastic material. Upon melting, at least a portion of this thermoplastic material migrates to the intersections of the respective member components, typically due to interparticle or interfiber capillary gradients. These intersections become bond sites for the thermoplastic material. When cooled, the thermoplastic materials at these intersections solidify to form the bond sites that hold the matrix of materials together.

Optional thermoplastic materials useful herein can be in any of a variety of forms including particulates, fibers, or combinations of particulates and fibers. Thermoplastic fibers are a particularly preferred form because of their ability to form numerous bond sites. Suitable thermoplastic materials can be made from ally thermoplastic polymer that can be melted at temperatures that will not extensively damage the materials that comprise absorbent member. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. One preferred thermoplastic binder fiber is PLEXAFIL® polyethylene microfibers (made by DuPont) that are also available as an about 20% blend with 80% cellulosic fibers sold under the tradename KITTYHAWK® (made by Weyerhaeuser Co.) Depending upon the desired characteristics for the resulting thermally bonded absorbent member, suitable thermoplastic materials include hydrophobic fibers that halve been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped b) typical textile means such as, for example, a stuffer box method or the gear crimp method to achieve a predominantly two-dimensional or "flat" crimp.

In the case of thermoplastic fibers, their length can vary depending upon the particular melt point and other properties desired for these fibers. Typically, these thermoplastic fibers have a length from about 0.3 to about 7.5 cm long, preferably from about 0.4 to about 3.0 cm long, and most preferably from al)out 0.6 to about 1.2 cm long. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers can have a decitex in the range from about 1.0 to about 20, preferably from about 1.4 to about 10, and most preferably from about 1.7 to about 3.3.

The compressive modulus of these thermoplastic materials, and especially that of the thermoplastic fibers, can also be important. The compressive modulus of thermoplastic fibers is affected not only by their length aid diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective absorbent members during preparation of the absorbent core.

Other materials generally known in the art may be included in the absorbent storage members, provided they are included at levels sufficiently low so the requisite capillary suction properties are achieved. Optional materials that may also be included in the storage members of the present invention include fibrous materials commonly combined with hydrogel-forming absorbent polymers. For example, wood-based fibers can be included, as can synthetic fibers. However, because such materials will tend to reduce the capillary suction capacity of the storage members comprising the high surface area material and the hydrogel-forming polymer, they will be included at relatively low levels, such that the members still provide the desired capillary suction absorbent capacity. Indeed, it may be preferred to exclude the use of such fibers, insofar as they add bulk and reduce capillary sorption capacity on a weight basis.

Numerous methods known in the art may be utilized for combining the hydrogel-forming polymer (or other osmotic absorbent) and the high surface area material. Of course, the physical form (e.g., fibrous, particulate, etc.) of the high surface area material and the hydrogel-forming absorbent polymer will dictate (or other osmotic absorbent), at least to some degree, what processes may be utilized for forming specific storage absorbent member embodiments.

In one embodiment, hydrogel-forming absorbent polymer particles may be affixed to fibrous material to prevent unwanted migration of the particles during manufacture, storage and/or wear. Attaching absorbent particles to molten polymeric material is disclosed in European Patent Publication EP 156,160, in which molten polymeric material is extruded so as to produce a stream of melt blown polymeric microfibres and, while they are still tacky, absorbent particles are directed therein so they adhere to the fibres.

The technique of entrapment of particulate absorbent materials in a meltblown web is disclosed in U.S. Pat. No. 4,923,454, in which microfiber-containing absorbent structures and absorbent articles in which wettable hydrophilic nylon meltblown microfibers and hydrogel-forming polymer particles are disclosed, and in U.S. Pat. No. 4,773,903 in which meltblown microfiber and hydrogel-forming polymer particles and crimped staple fibers and hydrophilizing agent are disclosed. The disclosure of these patents is incorporated by reference herein.

Entrapping high surface area materials and hydrogel-forming absorbent polymer by the technique generally described in U.S. Pat. No. 4,764,325, which is incorporated herein by reference, is also possible. The high surface area material and hydrogel-forming polymer may also be encapsulated by the techniques general y described in U.S. patent application Ser. No. 08/585,278, the disclosure of which is incorporated herein by reference.

While the basis weight of the storage absorbent members of the present invention is not critical and will vary depending on the end-use of the member (i.e., incorporation into, e.g., a feminine hygiene product, an infant diaper, an adult incontinent product, a bandage), the members will typically have a basis weight of from about 5 to about 3000 g/m², or from about 40 to about 2500 g/m², or from about 100 to about 2000 g/m², or from about 150 to about 1500 g/m², or from about 250 to about 1000 g/m².

Figure 9:
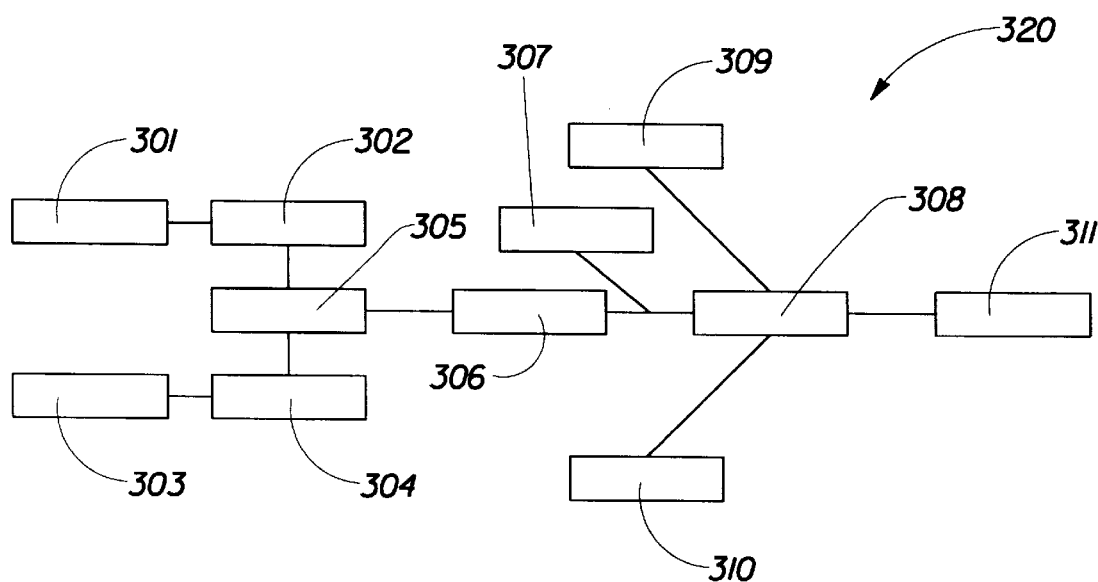
FIG. 9 is a schematic view of an apparatus for forming a representative storage absorbent member of the present invention, where the member comprises a blend of particulate polymeric foam and particulate hydrogel-forming absorbent polymer.

As indicated, particularly preferred storage absorbent members that comprise and osmotic absorbent are those where high capillary suction polymeric foam is used as the high surface area material. In one embodiment, the polymeric foam is in the form of particles and is mixed with particulate hydrogel-forming absorbent polymer to make a homogeneous blend. FIG. 9 is a schematic diagram of an apparatus 320 for making such a homogeneous blend. Referring to FIG. 9, an absorbent member is prepared by introducing particulate polymeric foam from first feed supply 301 to a first metering device 302 (optionally, device 302 is a fluidized bed lost weight system which will control the amount of particulate foam metered to the line based on the weight difference from the device over a specified time) and introducing particulate hydrogel-forming polymer from second feed supply 303 to a second metering device 304 (optionally, device 304 is a weight and loss metering system commonly used in commercial manufacture of diapers and feminine hygiene products; for example a weight and loss system available from Acrison, Inc., Moonachi, N.Y. This step sets the basis weight of the hydrogel-forming absorbent polymer in the product.) The polymeric foam particles and hyrdogel-forming polymer particles are introduced into a single mixing chamber 305. Within the mixing chamber 305 a homogeneous blend of the two components is created. This mixture is then transported with an airstream 306 (using, e.g., a venturi eductor to increase the kinetic energy of the particles) through a fibrous adhesive stream originating from 307. Alternatively, the pieces of foam and hydrogel-forming polymer can also be "agglomerated" by any technique capable of producing a relatively homogeneous mixture, bonding or binding the material together, obtaining a free flowing blend to be introduced into airstream 306. The fibrous adhesive stream may be introduced via a melt blown adhesive system such as that available from J&M Laboratories, Inc., Dawsonville, Ga. This fibrous adhesive stream entangles the particles of polymeric foam and hydrogel-forming polymer to form a composite shown generally as 308. (Homogeneous mixing is assumed to be feasible in the inlet chamber of, e.g., a Fox (Dover, N.J.) venturi eductor. If homogeneous mixing in chamber 305 is not feasible, two separate transport streams may be required to combine the particulate foam and the particulate hydrogel-forming absorbent polymer with fibrous adhesive delivered from 307.) The composite 308 is then optionally positioned between a first web introduced via device 309 and a second web introduced via device 310 to form an absorbent storage member 311. The entire absorbent storage member 311 may then be compressed (e.g., using a rotary nip) to achieve the target density and caliper of the member. In one specific embodiment, one of the webs is preferably a liquid distribution material described above, and the other web is a core cover material such as a non-woven fabric or high-loft which would be placed next to an absorbent article backsheet.

A similar process to that described in the preceding paragraph can be used to combine high surface area fibrets with an osmotic absorbent (e.g., particulate hydrogel-forming absorbent polymer). That is, the fibrets may be introduced via a device similar to first feed supply 301 shown in FIG. 10. Other well known methods for combining fibers and hydrogel-forming polymers may be employed. A representative means for preparing such a composite is described in Example 1 below.

An alternate process for mixing and acceleration of the particulate polymeric foam and hydrogel-forming polymer utilizes electrostatic forces. In this embodiment, the two types of materials are "charged" to cause an attractive force between them. This force is used to create the homogeneous blend of the two, and potentially will create the motive force to accelerate the blend through the adhesive stream, thus eliminating one of the process air streams.

Figure 10:
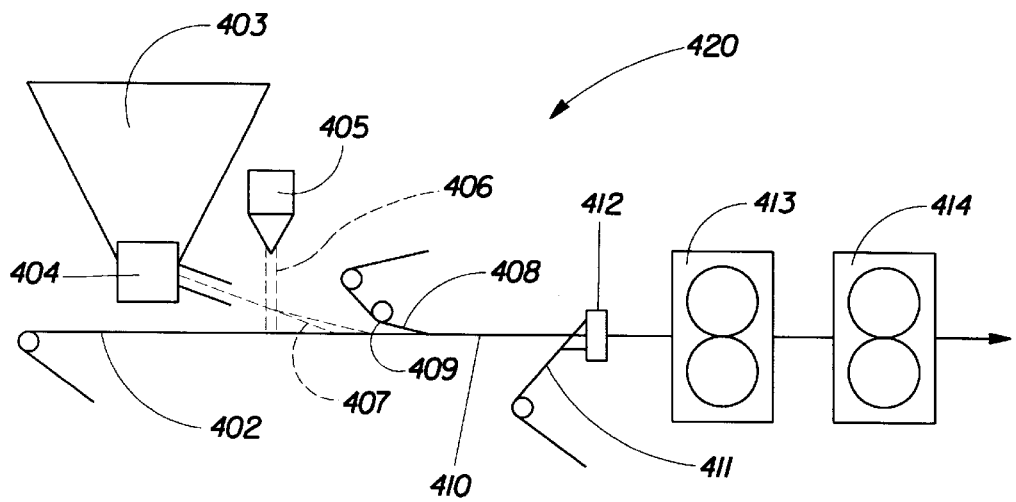
FIG. 10 is a schematic view of another apparatus for forming a representative storage absorbent member of the present invention.
Figure 11:
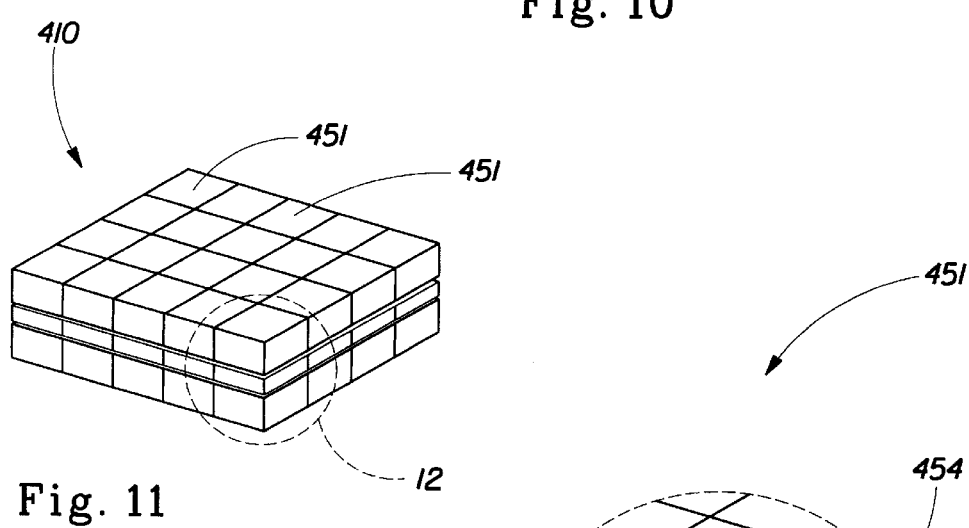
FIG. 11 is perspective view of a storage absorbent member made using the apparatus depicted in FIG. 10.

In another preferred embodiment, particulate hydrogel-forming absorbent polymer is positioned between two sheets of polymeric foam material. This layered combination is then manipulated (e.g., cut through its thickness) in the machine and/or the cross direction to cause the sheets to separate into strips or, pieces, to provide an storage absorbent member comprised of small sections of the layered combination. (It is noted that the layered structure formed prior to cutting is also useful as a storage absorbent member and may provide benefits in terms of manufacture on a commercial scale. However, Applicants have found that further processing provides a storage absorbent member having particularly high capillary sorption absorbent capacity at high suction heights.) FIG. 10 depicts an apparatus 420 for making such a layered combination and FIG. 11 depicts the layered, sectioned combination that may be used as absorbent storage member of the present invention. Referring to apparatus 420 shown in FIG. 10, a first tensioned sheet of polymeric foam material 402 is metered via any means well known in the art. Separately, a stream of particulate hydrogel-forming absorbent polymer is metered from metering device 403 (optionally, device 403 is a weight and loss metering system commonly used in commercial manufacture of diapers and feminine hygiene products; for example a metering system available from Acrison, Inc. Hydrogel-forming polymer is metered into an accelerator 404 (e.g., a venturi eductor or a fluidized bed such as the Flexispray™ type system available from Nordson, Inc., Atlanta, Ga.) where it is transported in an airstream toward a fibrous (preferably hydrophilic) adhesive 406 (e.g., Cycloflex™ 34-5652 from National Starch, Bridgewater, N.J.) delivered from 405. The fibrous adhesive entangles the particles of hydrogel-forming polymer and immobilizes them, forming a mixture 407. Slightly downstream from the location where the fibrous adhesive and hydrogel-forming polymer are combined, a second tensioned sheet of polymeric foam 408 is metered. The momentum of the particle/adhesive mixture 407 carries the mixture into a nip point 409 where sheets 402 and 408 combined. This results in a layered composite 410 comprising a layer of hydrogel-forming polymer and adhesive sandwiched between two sheets of polymeric foam material. Composite 410 is then combined with a non-woven material 411 and the combination is introduced to folding board 412, which folds (preferably an "e" fold) non-woven 411 around the composite 410. (The non-woven material provides composite integrity during subsequent reforming to operations and also provides additional integrity in the final structure.) The wrapped composite is then introduced to a first reforming device 413 and a second reforming device 414. In reforming devices 413 and 414 the wrapped composite is selectively slit by applying planes of shear in multiple directions. The planes of shear fracture the wrapped composite into columns of polymer foam and hydrogel-forming polymer/fibrous adhesive layers. The reforming operation also reduces the basis weight of the composite, including the non-woven, about the shear planes.

Figure 12:
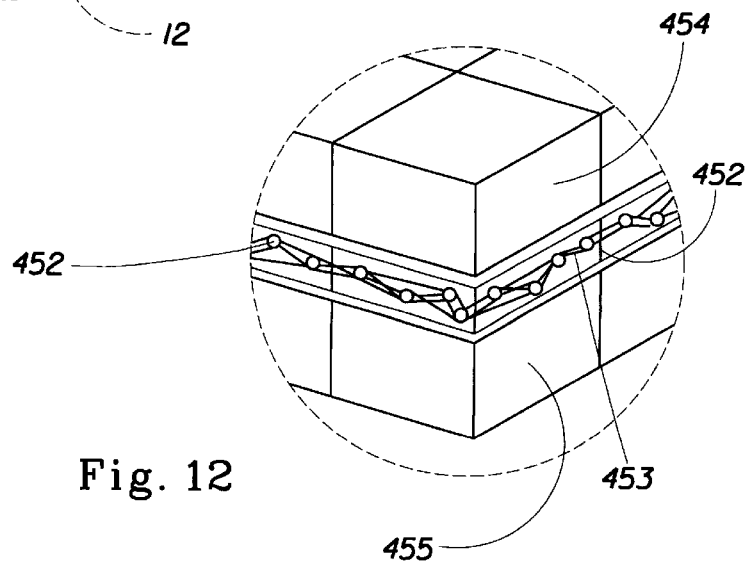
FIG. 12 is an expanded perspective view of a portion of the storage absorbent member depicted in FIG. 11.

To fully understand the physical nature of a preferred composite formed in the above operation, FIG. 11 shows composite 410 in detail (without depicting the nonwoven wrap), after it has been subjected to reformation in devices 413 and 414. In this embodiment, one of the reforming devices has cut the composite through its entire thickness into several strips in the cross-direction, while the other reforming device has cut the composite through its entire thickness in the machine direction. The result is a composite comprised of numerous discrete layered columns shown as 451. One of these columns 451 is shown in an expanded view in FIG. 12, which more clearly shows that each column 451 comprises hydrogel-forming polymer particles, shown as 452, and fibrous adhesive, shown as 453, sandwiched between "cubes" 454 and 455 of polymeric foam material. To enhance the interface between the hydrogel-forming absorbent polymer and the polymeric foam material, gentle mixing (e.g., application of shear forces) may be applied to composite 410 during and/or after reformation in devices 413 and 414.

V. Absorbent Articles

The high suction storage absorbent members of the present invention are particularly useful as the storage portion of the absorbent structures (e.g., absorbent cores or core elements) for various absorbent articles. By "absorbent article" herein is meant a consumer product that is capable of absorbing significant quantities of urine, menses, or other fluids (i.e., liquids), such as aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, bandages, and the like. The storage absorbent members herein are particularly suitable for use in articles such as diapers, incontinence pads or garments, clothing shields, bandages, and the like.

In its simplest form, an absorbent article of the present invention need only include the storage absorbent member of the present invention, but will typically include a backing sheet, typically relatively liquid-impervious, and the high suction storage member. In another simple form, the absorbent article need only include a backing sheet, an acquisition material, and the high suction storage member. The components will be associated such that the acquisition material is positioned so as to acquire the liquid discharge of the wearer of the absorbent article. The high suction member described herein is located so as to be in liquid communication with tie acquisition member, or any optional liquid distribution member that is in liquid or capillary communication with the acquisition member. Liquid impervious backing sheets can comprise any material, for example polyethylene or polypropylene, having a thickness of about 1.5 mils (0.038 mm), which will help retain liquid within the absorbent article.

More conventionally, these absorbent articles will also include a liquid-pervious topsheet element that covers the side of the absorbent article that touches the skin of the wearer. In this configuration, the article includes an absorbent core comprising one or more storage absorbent members of the present invention positioned between the backing sheet and the topsheet. Liquid-pervious topsheets can comprise any material such as polyester, polyolefin, rayon and the like that is substantially porous and permits body liquid to readily pass there through and into the underlying absorbent core. The topsheet material will preferably have no propensity for holding aqueous liquids in the area of contact between the topsheet and the wearer's skin.

In addition to the storage absorbent member of the present invention, the absorbent core of the absorbent articles herein can also comprise other, e.g., conventional, elements or materials. In one embodiment involving a combination of the absorbent member herein and other absorbent materials, the absorbent articles can employ a multi-layer absorbent core configuration where a core layer containing one or more absorbent storage members of the present invention can be used in combination with one or more additional separate core layers comprising other absorbent structures or materials. These other absorbent structures or materials, for example, can include air-laid or wet-laid webs of wood pulp or other cellulosic fibers. These other absorbent structures can also comprise foams, e.g., absorbent foams or even sponges useful as liquid acquisition/distribution components such as those disclosed in U.S. Pat. No. 5,563,179 (Stone et al.) issued Oct. 8, 1996, the disclosure of which is incorporated herein by reference.

Another preferred embodiment entails a further separation of the various absorbent core elements. This preferred absorbent core comprises an acquisition layer only around the crotch region of the wearer to manage the initial rapid liquid gush. A distribution layer is positioned vertically to the front and back of the acquisition layer so as to wick the liquid out of the crotch region. The storage layer is positioned in a position near the front and rear waist regions, and is in contact only with the distribution material. The storage absorbent member(s) then must be able to absorb the liquid from the distribution layer, overcoming both the force due to gravity and that due to the desorption pressures of the distribution material. The product so depicted removes liquid from the crotch region within the time provided between insults, leaving the acquisition region relatively dry and ready for further uptake of liquid. This further maintains the shape of the garment and keeps the crotch area relatively dry for better skin health. See, e.g., co-pending U.S. patent application Ser. No. 08/825,072, filed Mar. 27, 1997 by G. Young et al., co-pending U.S. patent application Ser. No. 081825,071, filed Mar. 27, 1997 by G. La Von et al., and U.S. Pat. No. 5,827,253 (Young et al.), issued Oct. 27, 1998, which are incorporated by reference herein.

FIG. 1 shows a preferred embodiment of a diaper 60 in which the topsheet 61 and the backsheet 62 are co-extensive and have length and width dimensions generally larger than those of the absorbent core 28. The topsheet 61 is joined with and superimposed on the backsheet 62 thereby forming the periphery of the diaper 60. The periphery defines the outer perimeter or the edges of the diaper 60.

The topsheet 61 is compliant, soft feeling, and non-irritating to the wearer's skin. Further, the topsheet 61 is liquid pervious permitting liquids to readily penetrate through its thickness. A suitable topsheet 61 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Typically, the topsheet 61 is made of a hydrophobic material, treated to be initially hydrophilic, to isolate the wearer's skin from liquids in the storage absorbent member 10. The hydrophilic treatment causes initial wettability of the topsheet so liquid discharges can penetrate the topsheet. A particularly preferred topsheet 61 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 61. For example, the topsheet 61 can be woven, nonwoven, spunbonded, carded, or the like. A preferred topsheet is carted, and thermally bonded by means well known to those skilled in the fabrics art Preferably, the topsheet 61 has a weight from about 18 to about 25 grams per square meter, a minimum dry tensile strength of at least about 400 grams per centimeter in the machine direction, and a wet tensile strength of at least about 55 grams per centimeter in the cross-machine direction.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent core itself could be made of liquid pervious, soft, compliant, non-irritating materials that substitute for a separate topsheet. Such an absorbent core would only need to be used in combination with a backsheet to provide for comfort and absorbency in an absorbent article.

The backsheet 62 is impervious to liquids and is preferably manufactured from a thin plastic film, although other flexible liquid impervious materials may also be used. The backsheet 62 prevents the exudates absorbed and contained in the storage absorbent member 10 from wetting articles which contact the diaper 60 such as bed sheets and undergarments. Preferably, the backsheet 62 is polyethylene film having a thickness from about 0.012 mm (0.5 mil) to about 0.051 centimeters (2.0 mils), although other flexible, liquid impervious materials can be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 62 is preferably embossed and/or matte finished to provide a more cloth-like appearance. Further, the backsheet 62 may be "breathable," permitting vapors to escape from the absorbent core 28 while still preventing exudates from passing through the backsheet 62. It is contemplated that a backsheet that is highly breathable but substantially impervious to liquid may be desirable for certain absorbent articles. The size of the backsheet 62 is dictated by the size of the absorbent core 28 and the exact diaper design selected. In a preferred embodiment, the backsheet 62 has a modified hourglass-shape extending beyond the absorbent core 28 a minimum distance of at least about 1.3 centimeters to at least about 2.5 centimeters (about 0.5 to about 1.0 in.) around the entire diaper periphery.

The topsheet 61 and the backsheet 62 are joined together in any suitable manner. As used herein, the term "joined" encompasses configurations whereby the topsheet 61 is directly joined to the backsheet 62 by affixing the topsheet 61 directly to the backsheet 62, and configurations whereby the topsheet 61 is indirectly joined to the backsheet 62 by affixing the topsheet 61 to intermediate members which in turn are affixed to the backsheet 62. In a preferred embodiment, the topsheet 61 and the backsheet 62 are affixed directly to each other in the diaper periphery by attachment means (not shown) such as an adhesive or any other attachment means as known in the art. For example, a uniform continuous layer of adhesive, a patterned layer of adhesive, or an array of w separate lines or spots of adhesive can be used to affix the topsheet 61 to the backsheet 62.

Tape tab fasteners 65 are typically applied to the waistband region 63 of the diaper 60 to provide a fastening means for holding the diaper on the wearer. The tape tab fasteners 65 depicted are representative only. The tape tab fasteners can be any of those well known in the art, such as the fastening tape disclosed in U.S. Pat. No. 3,848,594 (Buell), issued Nov. 19, 1974, which is incorporated by reference. These tape tab fasteners or other diaper fastening means are typically applied near the corners of the diaper 60.

Elastic members 69 are disposed adjacent the periphery of the diaper 60, preferably along each longitudinal edge 64, so that the elastic members tend to draw and hold the diaper 60 against the legs of the wearer. Additionally, elastic members 67 can be disposed adjacent either or both of the waistband regions 63 of the diaper 60 to provide a waistband as well as or rather than leg cuffs. For example, a suitable waistband is disclosed in U.S. Pat. No. 4,515,595 (Kievit et al.), issued May 7, 1985, which is incorporated by reference. In addition, a method and apparatus suitable for manufacturing a disposable diaper having elastically contractible elastic members is described in U.S. Pat. No. 4,081,301 (Buell), issued Mar. 28, 1978, which is incorporated by reference.

The elastic members are secured to the diaper 60 in an elastically contractible condition so that in a normally unrestrained configuration, the elastic members effectively contract or gather the diaper 60. The elastic members can be secured in an elastically contractible condition in at least two ways. For example, the elastic members can be stretched and secured while the diaper 60 is in an uncontracted condition. Alternatively, the diaper 60 can be contracted, for example, by pleating, and the elastic members secured and connected to the diaper 60 while the elastic members are in their unrelaxed or unstretched condition. The elastic members may extend along a portion of the length of the diaper 60. Alternatively, the elastic members can extend the entire length of the diaper 60, or any other length suitable to provide an elastically contractible line. The length of the elastic members is dictated by the diaper design.

In use, the diaper 60 is applied to a wearer by positioning one waistband region under the wearer's back, and drawing the remainder of the diaper 60 between the wearer's legs so that the other waistband region is positioned across the front of the wearer. The tape-tab 65 or other fasteners are then secured preferably to outwardly facing areas of the diaper 60. In use, disposable diapers or other absorbent articles incorporating the storage absorbent members of the present invention tend to more efficiently store liquids and to remain dry due to the high absorbent capacity and high suction capacity of the absorbent members.

When used as an absorbent core in a disposable diaper 60, a preferred embodiment of the core 28 according to the present invention is positioned such that an acquisition strip 52 is in liquid communication with topsheet 61, and serves to quickly acquire and partition body exudates from the wearer's body to an absorptive distribution strip 51. Adhesive bonding of acquisition strip 52 to topsheet 61 may enhance the liquid communication by providing interfacial bonding and preventing topsheet separation from impeding liquid flow. The distribution material 51 moves liquid in the x and y dimensions of the core 28 and is subsequently desorbed by the liquid storage component, shown generally as 10, which is a storage absorbent member of the present invention. While components 52 and 51 are shown generally as being rectilinear and of equal size, other shapes and size relationships may be utilized. As shown, the generally rectilinear components have a width 53 corresponding to a suitable width for the crotch area 66 of a disposable diaper. As well, the length of the respective core components may be varied to provide a suitable fit for various wearer sizes.

As is shown in FIG. 1, storage absorbent member 10 can comprise two separate storage absorbent member 20 and 30 such that there is no storage absorbent member element located in the liquid discharge region of the diaper. Because such an storage absorbent member 10 has little or no liquid storage material (it should be recognized that the distribution material 51 may have significant storage capacity and will contain liquid at least until it is desorbed by the higher suction storage material) in the center of the core (corresponding to the crotch or liquid discharge region of the core), articles containing such cores may provide improved fit and wearer comfort both when the article is dry and after it has received several loadings of body liquid. See, e.g., co-pending U.S. patent application Ser. No. 08/825,072, filed Mar. 27, 1997 by G. Young et al., co-pending U.S. patent application Ser. No. 08/825,071, filed Mar. 27, 1997 by G. La Von et al., and U.S. Pat. No. 5,827,253 (Young et al.), issued Oct. 27, 1998. FIG. 2a depicts a blown-apart view of absorbent core 28 having two separated elements 20 and 30, each of which consist of a storage absorbent member of the present invention. Front panel 20 generally corresponds to the portion of the disposable diaper worn in the front of the wearer. Similarly, the back panel 30 corresponds to the portion of the disposable diaper worn in the back of the wearer.

Alternatively, storage absorbent member 10 may be a unitary layer(s) (i.e., where the dashed lines 70 in FIG. 1 indicate that storage absorbent member 10 is included in the liquid discharge region of the article) of storage absorbent material of the present invention. Such an embodiment of an absorbent core 28 is depicted in FIG. 2b.

In one embodiment, acquisition strip 52 will be a liquid handling layer, positioned in the liquid discharge region of the wearer of the article, in the form of a high loft nonwoven, but is preferably in the form of a liquid acquisition layer comprising a layer of modified cellulosic fibers, e.g., stiffened curled cellulosic fibers, and optionally up to about 10% by weight of this liquid acquisition/distribution layer of polymeric gelling agent. In a preferred embodiment, acquisition strip 52 will comprise a high loft chemically bonded polyethylene terephthalate (PET) nonwoven layer (e.g., having a basis weight of about 42 g/m$^2$) overlying a layer of stiffened curled cellulosic fibers (e.g., available from Weyerhauser Co. WA. as CMC®; also available from The Procter & Gamble Co., Paper Technology Division, Cincinnati, Ohio), such that the PET nonwoven layer is positioned between the stiffened curled cellulosic fibers and the topsheet. The modified cellulosic fibers used in the liquid acquisition layer 52 of such a preferred absorbent article are preferably wood pulp fibers that have been stiffened and curled by means of chemical and/or thermal treatment. Such modified cellulosic fibers are of the same type as are employed in the absorbent articles described in U.S. Pat. No. 4,935,022 (Lash et al.), issued Jun. 19, 1990, which is incorporated herein by reference. A preferred embodiment is one where the liquid distribution layer 51 is as described in co-pending U.S. patent application Ser. No. 09/042,418, filed Mar. 13, 1998 by DesMarais et al. titled "ABSORBENT MATERIALS FOR DISTRIBUTING AQUEOUS LIQUIDS" (P&G Case 7051) or U.S. Pat. No. 5,800,416 (Seger et al.), issued Sep. 1, 1998, each of which is incorporated by reference herein. [In a preferred embodiment utilizing the fibrous distribution materials described in copending U.S. Patent No. 5,800,416, the distribution material is passed through at least two rolls each with circumferential ridges and grooves, which are run at such a close tolerance that the web undergoes permanent deformation. Similar processes have been developed for treating stretch laminate materials and are described in U.S. Pat. No. 5,167,897 (Weber) relating to stretch materials. Essentially, this process provides mechanical treatment of the web.] This optional liquid distribution layer is typically positioned between the (upper) liquid-handling (e.g., liquid acquisition material) and the (lower) high suction storage absorbent layer and is in liquid communication therewith. Absorbent articles that can utilize the storage absorbent members of the present invention in a lower liquid storage layer underlying an upper liquid acquisition/distribution layer containing stiffened curled cellulosic fibers are described in greater detail in the U.S. Pat. No. 5,147,345 (Young et al.), issued Sep. 15, 1992.

As referred to herein, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, catamenial pads, sanitary napkins, tampons, bandages, facial tissues, paper towels, and the like.

VI. Test Methods

A. Capillary Sorption

Purpose

The purpose of this test is to measure the capillary sorption absorbent capacity, as a function of height, of storage absorbent members of the present invention. (The test is also used to measure the capillary sorption absorbent capacity, as a function of height, of the high surface area materials—i.e., without osmotic absorbent, such as hydrogel-forming absorbent polymer, (if any is present) or other optional materials utilized in the absorbent member. Nonetheless, the discussion that follows discusses the Capillary Sorption method as it pertains to measuring an entire storage absorbent member.) Capillary sorption is a fundamental property of any absorbent that governs how liquid is absorbed into the absorbent structure. In the Capillary Sorption experiment, capillary sorption absorbent capacity is measured as a function of fluid pressure due to the height of the sample relative to the test fluid reservoir.

The method for determining capillary sorption is well recognized. See Burgeni, A. A. and Kapur, C., "Capillary Sorption Equilibria in Fiber Masses," Textile Research Journal, 37 (1967), 356–366; Chatterjee, P. K., Absorbency, Textile Science and Technology 7, Chapter II, pp 29–84, Elsevier Science Publishers B. V, 1985; and U.S. Pat. No. 4,610,678, issued Sep. 9, 1986 to Weisman et al. for a discussion of the method for measuring capillary sorption of absorbent structures. The disclosure of each of these references is incorporated by reference herein.

Principle

A porous glass frit is connected via an uninterrupted column of fluid to a fluid reservoir on a balance. The sample is maintained under a constant confining weight during the experiment. As the porous structure absorbs fluid upon demand, the weight loss in the balance fluid reservoir is recorded as fluid uptake, adjusted for uptake of the glass frit as a function of height and evaporation. The uptake or capacity at various capillary suctions (hydrostatic tensions or heights) is measured. Incremental absorption occurs due to the incremental lowering of the frit (i.e., decreasing capillary suction).

Time is also monitored during the experiment to enable calculation of initial effective uptake rate (g/g/h) at a 200 cm height.

Reagents

Test Liquid: Synthetic urine is prepared by completely dissolving the following materials in distilled water.

| Compound | F.W. | Concentration (g/L) |
|---|---|---|
| KCl | 74.6 | 2.0 |
| $Na_2SO_4$ | 142 | 2.0 |
| $(NH_4)H_2PO_4$ | 115 | 0.85 |
| $(NH_4)_2HPO_4$ | 132 | 0.15 |
| $CaCl_2 \cdot 2H_2O$ | 147 | 0.25 |
| $MgCl_2 \cdot 6H_2O$ | 203 | 0.5 |

General Description of Apparatus Set Up

Figure 8A:
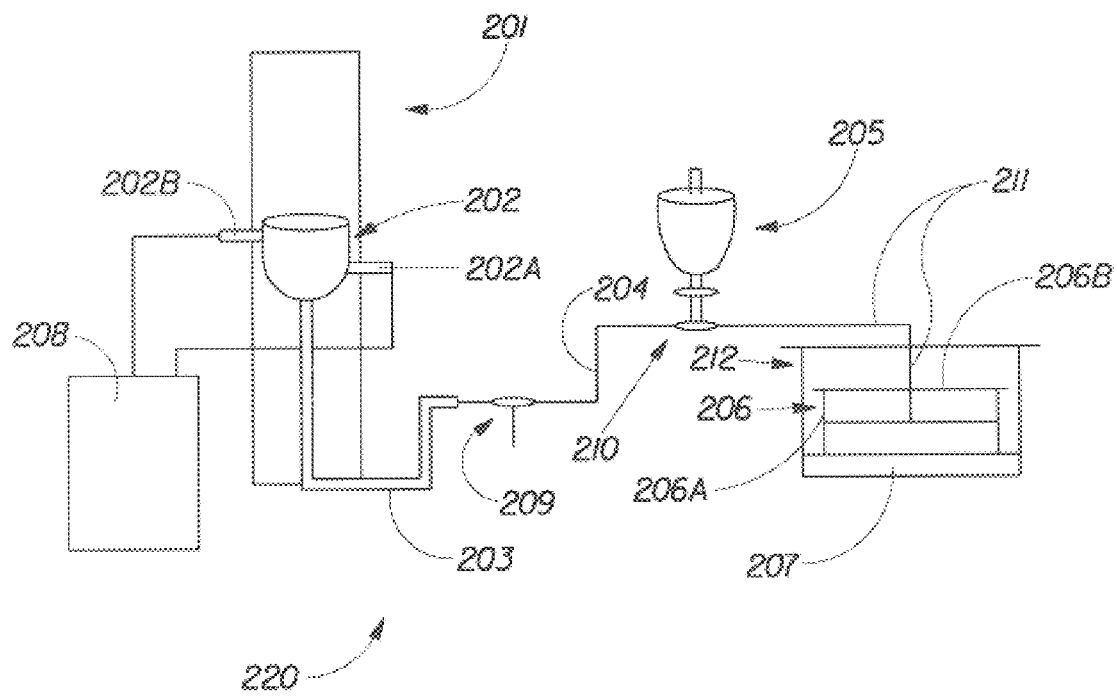
FIG. 8A represents a schematic view of an apparatus for measuring capillary sorption absorbent capacity of an absorbent member.

The Capillary Sorption equipment, depicted generally as 220 in FIG. 8A, used for this test is operated under TAPPI conditions (50% RH, 25° C). A test sample is placed on a glass frit shown in FIG. 8A as 202 that is connected via a continuous column of test liquid (synthetic urine) to a balance liquid reservoir, shown as 206, containing test liquid. This reservoir 206 is placed on a balance 207 that is interfaced with a computer (not shown). The balance should be capable of reading io 0.001 g; such a balance is available from Mettler Toledo as PR1203 (Hightstown, N.J.). The glass frit 202 is placed on a vertical slide, shown generally in FIG. 8A as 201, to allow vertical movement of the test sample to expose the test sample to varying suction heights. The vertical slide may be a rodless actuator which is attached to a computer to record suction heights and corresponding times for measuring liquid uptake by the tenet sample. A preferred rodless actuator is available from Industrial Devices (Novato, Calif.) as item 202X4X34N-1D4B-84-P-C-S-E, which may be powered by motor drive ZETA 6104-83-135, available from CompuMotor (Rohnert, Calif.). Where data is measured and sent from actuator 201 and balance 207, capillary sorption absorbent capacity data may be readily generated for each test sample. Also, computer interface to actuator 201 may allow for controlled vertical movement of the glass frit 202. For example, the actuator may be directed to move the glass frit 202 vertically only after "equilibrium" (as defined below) is reached at each suction height.

The bottom of glass frit 202 is connected to Tygon® tubing 203 that connects the frit 202 to three-way drain stopcock 209. Drain stopcock 209 is connected to liquid reservoir 205 via glass tubing 204 and stopcock 210. (The stopcock 209 is open to the rain only during cleaning of the apparatus or air bubble removal.) Glass tubing 211 connects fluid reservoir 205 with balance fluid reservoir 206. via stopcock 210. Balance liquid reservoir 206 consists of a light weight 12 cm diameter glass dish 206A and cover 206B. The cover 206B has a hole through which glass tubing 211 contacts the liquid in the reservoir 206. The glass tubing 211 must not contact the cover 206B or an unstable balance reading will result and the test sample measurement cannot be used.

The glass frit diameter must be sufficient to accommodate the piston/cylinder apparatus, discussed below, for holding the test sample. The glass frit 202 is jacketed to allow for a constant temperature control from a heating bath. The frit is a 350 mL fritted disc funnel specified as having 4 to 5.5 μm pores, available from Corning Glass Co. (Corning, N.Y.) as #36060-350F. The pores are fine enough to keep the frit surface wetted at capillary suction heights specified (the glass frit does not allow air to enter the continuous column of test liquid below the glass frit).

As indicated, the frit 202 is connected via tubing to fluid reservoir 205 or balance liquid reservoir 206, depending on the position of three-way stopcock 210.

Glass frit 202 is jacketed to accept water from a constant temperature bath. This will ensure that the temperature of the glass frit is kept at a constant temperature of 88° F. (31° C.) during the testing procedure. As is depicted in FIG. 8A, the glass frit 202 is equipped with an inlet port 202A and outlet port 202B, which make a closed loop with a circulating heat bath shown generally as 208. (The glass jacketing is not depicted in FIG. 8A. However, the water introduced to the jacketed glass frit 202 from bath 208 does not contact the test liquid and the test liquid is not circulated through the constant temperature bath. The water in the constant temperature bath circulates through the jacketed walls of the glass frit 202.)

Reservoir 206 and balance 207 are enclosed in a box to minimize evaporation of test liquid from the balance reservoir and to enhance balance stability during performance of the experiment. This box, shown generally as 212, has a top and walls, where the top has a hole through which tubing 211 is inserted.

Figure 8B:
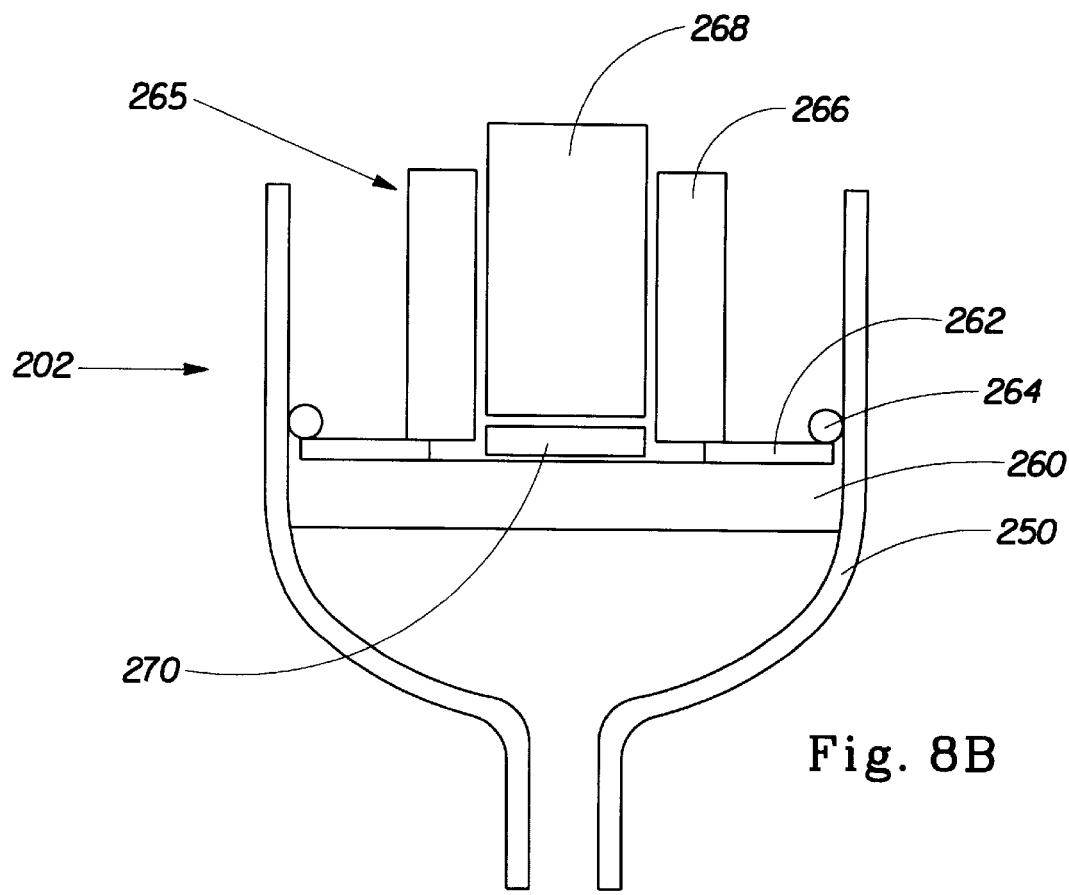
FIG. 8B represents a cross-sectional, close-up view of the glass frit shown generally in FIG. 8A.

The glass frit 202 is shown in more detail in FIG. 8B. FIG. 8B is a cross-sectional view of the glass frit, shown without inlet port 202A and outlet port 202B. As indicated, the glass frit is a 350 mL flitted disc funnel having specified 4 to 5.5 μm pores. Referring to FIG. 8B, the glass frit 202 comprises a cylindrical jacketed funnel designated as 250 and a glass frit disc shown as 260. The glass frit 202 further comprises a cylinder/piston assembly shown generally as 265 (which comprises cylinder 266 and piston 268), which confines the test sample, shown as 270, and provides a small confining pressure to the test sample. To prevent excessive evaporation of test liquid from the glass frit disc 260, a Teflon ring shown as 262 is placed on top of the glass frit disc 260. The Teflon® ring 262 is 0.0127 cm thick (available as sheet stock from McMasterCarr as # 8569K16 and is cut to size) and is used to cover the frit disc surface outside of the cylinder 266, and thus minimizes evaporation from the glass frit. The ring outer diameter and inner diameter is 7.6 and 6.3 cm, respectively. The inner diameter of the Teflon® ring 262 is about 2 mm less than the outer diameter of cylinder 266. A Viton® O-ring (available from McMasterCarr as # AS568A-150 and AS563A-151) 264 is placed on top of Teflon® ring 262 to seal the space between the inner wall of cylindrical jacketed funnel 250 and Teflon® ring 262, to further assist in prevention of evaporation. If the O-ring outer diameter exceeds the inner diameter of cylindrical jacketed funnel 250, the O-ring diameter is reduced to fit the funnel as follows: the O-ring is cut open, the necessary amount of O-ring material is cut off, and the O-ring is glued back together such that the O-ring contacts the inner wall of the cylindrical jacketed funnel 250 all around its periphery.

Figure 8C:
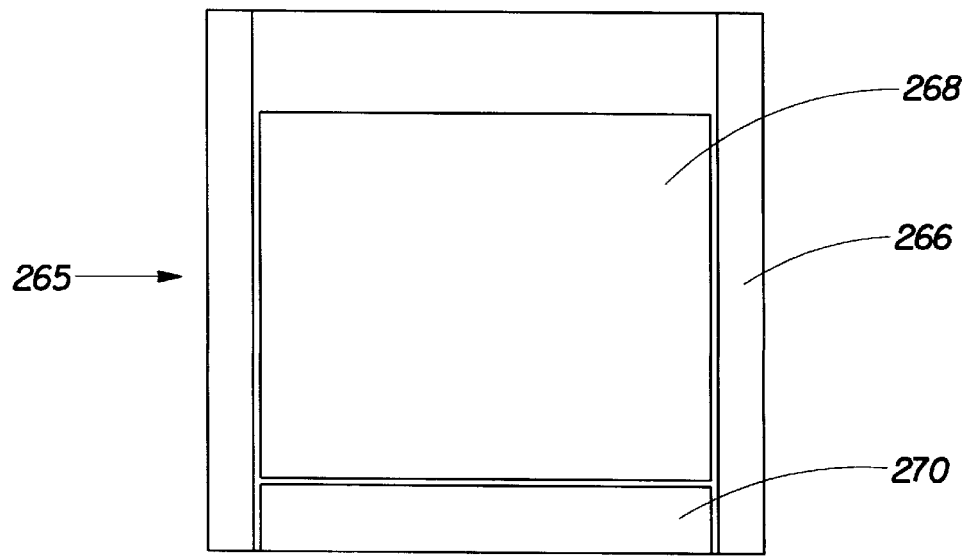
FIG. 8C represents a cross-sectional, close-up view of the cylinder/piston assembly of the glass frit shown in FIG. 8B.
Figure 8D:
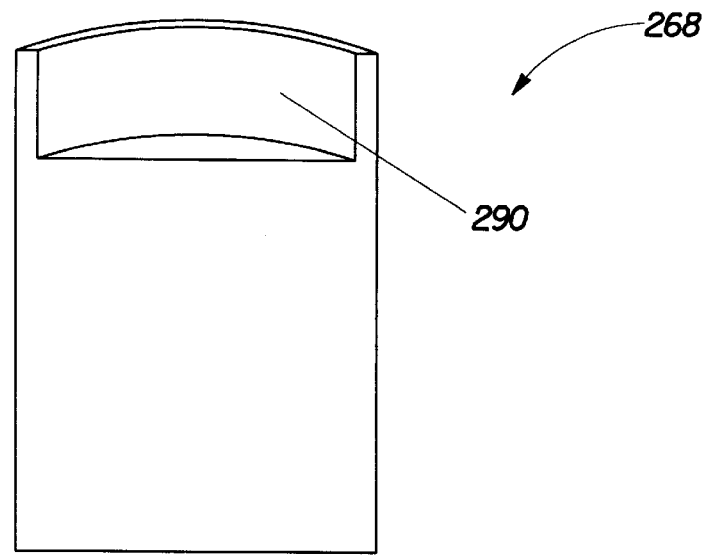
FIG. 8D represents a cross-sectional, close-up view of the piston aspect of the cylinder/piston assembly shown in FIG. 8C.

As indicated, a cylinder/piston assembly shown generally in FIG. 8B as 265 confines the test sample and provides a small confining pressure to the test sample 270. Referring to FIG. 8C, assembly 265 consists of a cylinder 266, a cup-like Teflon® piston indicated by 268 and, when necessary, a weight or weights (not shown) that fits inside piston 268. (Optional weight will be used when necessary to adjust the combined weight of the piston and the optional weight so a confining pressure of 0.2 psi is attained depending on the test sample's dry diameter. This is discussed below.) The cylinder 266 is Lexan® bar stock and has the following dimensions: ani outer diameter of 7.0 cm, an inner diameter of 6.0 cm and a height of 6.0 cm. The Teflon® piston 268 has the following dimensions: an outer diameter that is 0.02 cm less than the inner diameter of cylinder 266. As shown in FIG. 8D, the end of the piston 268 that does not contact the test sample is bored to provide a 5.0 cm diameter by about 1.8 cm deep chamber 290 to receive optional weights (dictated by the test sample's actual dry diameter) required to attain a test sample confining pressure of 0.2 psi (1.4 kPa). In other words, the total weight of the piston 268 and any optional weights (not shown in figures) divided by the test sample's actual diameter (when dry) should be such that a confining pressure of 0.2 psi is attained. Cylinder 266 and piston 268 (and optional weights) are equilibrated at 31° C. for at least 30 minutes prior to conducting the capillary sorption absorbent capacity measurement.

A non-surfactant treated or incorporated apertured film (14 cm×14 cm) (not shown) is used to cover the glass frit 202 during Capillary Sorption experiments to minimize air destablization around the sample. Apertures are large enough to prevent condensation from forming on the underside of the film during the experiment.

Test Sample Preparation

The test sample can be obtained by punching out a 5.4 cm diameter circular-shaped structure from a storage absorbent member, using an arch punch. When the member is a component of an absorbent article, other components of the article must be removed prior to testing. In those situations where the member cannot be isolated from other components of the article without significantly altering its structure (e.g., density, relative disposition of the component materials, physical properties of constituent materials, etc.) or where the member is not a component or an absorbent article, the test sample is prepared by combining all the materials that constitute the member such that the combination is representative of the member in question.

The dry weight of the test sample (used below to calculate capillary sorption absorbent capacity) is the weight of the test sample prepared as above under ambient conditions.

Experimental Set Up

1. Place a clean, dry glass frit 202 in a funnel holder attached to the vertical slide 201. Move the funnel holder of the vertical slide such that the glass frit is at the 0 cm height.
2. Set up the apparatus components as shown in FIG. 8A, as discussed above.
3. Place 12 cm diameter balance liquid reservoir 206 on the balance 207. Place plastic lid 206B over this balance liquid reservoir 206 and a plastic lid over the balance box 212 each with small holes to allow the glass tubing 211 to fit through. Do not allow the glass tubing to touch the lid 206B of the balance liquid reservoir or an unstable balance reading will result and the measurement cannot be used.
4. Stopcock 210 is closed to tubing 204 and opened to glass tubing 211. Fluid reservoir 205, previously filled with test fluid, is opened to allow test fluid to enter tubing 211, to fill balance fluid reservoir 206.
5. The glass frit 202 is leveled and secured in place. Also, ensure that the glass frit is dry.
6. Attach the Tygon® tubing 203 to stopcock 209. (The tubing should be long enough to reach the glass frit 202 at its highest point of 200 cm with no kinks.) Fill this Tygon® tubing with test liquid from liquid reservoir 205.
7. Attach the Tygon® tubing 203 to the level glass frit 202 and then open stopcock 209 and stopcock 210 leading from fluid reservoir 205 to the glass frit 202. (Stopcock 210 should be closed to glass tubing 211.) The test liquid fills the glass frit 202 and removes all trapped air during filling of the level glass frit. Continue to fill until the fluid level exceeds the top of the glass frit disc 260. Empty the funnel and remove all air bubbles in the tubing and inside the funnel. Air bubbles may be removed by inverting glass flit 202 and allowing air bubbles to rise and escape through the drain of stopcock 209. (Air bubbles typically collect on the bottom of the glass frit disc 260.) Relevel the frit using a small enough level that it will fit inside the jacketed funnel 250 and onto the surface of glass frit disc 260.
8. Zero the glass frit with the balance liquid reservoir 206. To do this, take a piece of Tygon® tubing of sufficient length and fill it with the test liquid. Place one end in the balance liquid reservoir 206 and use the other end to position the glass frit 202. The test liquid level indicated by the tubing (which is equivalent to the balance liquid reservoir level) is 10 mm below the top of the glass frit disc 260. If this is not the case, either adjust the amount of liquid in the reservoir or reset the zero position on the vertical slide 201.
9. Attach the outlet and inlet ports from the temperature bath 208 via tubing to the inlet and outlet ports 202A and 202B, respectively, of the glass frit. Allow the temperature of the glass frit disc 260 to come to 31° C. This can be measured by partially filling the glass flit with test liquid and measuring its temperature after it has reached equilibrium temperature. The bath will need to be set a bit higher than 31° C. to allow for the dissipation of heat during the travel of water from the bath to the glass frit.
10. The glass frit is equilibrated for 30 minutes.

Capillary Sorption Parameters

The following describes a computer program that will determine how long the glass frit remains at each height.

In the capillary sorption software program, a test sample is at some specified height from the reservoir of fluid. As indicated above, the fluid reservoir is on a balance, such that a computer can read the balance at the end of a known time interval and calculate the flow rate (Delta reading/time interval) between the test sample and reservoir. For purposes of this method, the test sample is considered to be at "equilibrium" when the flow rate is less than a specified flow rate for a specified number of consecutive time intervals. It is recognized that for certain material, actual equilibrium may not be reached when the specified "EQUILIBRIUM CONSTANT" is reached. The time interval is between readings is 5 seconds.

The number of readings in the delta table is specified in the capillary sorption menu as "EQUILIBRIUM SAMPLES". The maximum number of deltas is 500. The flow rate constant is specified in the capillary sorption menu as "EQUILIBRIUM CONSTANT".

The Equilibrium Constant is entered in units of grams/sec, ranging from 0.0001 to 100.000.

The following is a simplified example of the logic. The table shows the balance reading and Delta Flow calculated for each Time Interval.

Equilibrium Samples=3; Equilibrium Constant=0.0015

| Time Interval | Balance Value (g) | Delta Flow (g/sec) |
|---|---|---|
| 0 | 0 | |
| 1 | 0.090 | 0.0180 |
| 2 | 0.165 | 0.0150 |
| 3 | 0.225 | 0.0120 |
| 4 | 0.270 | 0.0090 |
| 5 | 0.295 | 0.0050 |
| 6 | 0.305 | 0.0020 |
| 7 | 0.312 | 0.0014 |
| 8 | 0.316 | 0.0008 |
| 9 | 0.318 | 0.0004 |

Delta Table

| Time | 0 | 1 | 2 | 3 | 4 | 5 | 6 | 7 | 8 | 9 |
|---|---|---|---|---|---|---|---|---|---|---|
| Delta1 | 9999 | 0.0180 | 0.0180 | 0.0180 | 0.0090 | 0.0090 | 0.0090 | 0.0014 | 0.0014 | 0.0014 |
| Delta2 | 9999 | 9999 | 0.0150 | 0.0150 | 0.0150 | 0.0050 | 0.0050 | 0.0050 | 0.0008 | 0.0008 |
| Delta3 | 9999 | 9999 | 9999 | 0.0120 | 0.0120 | 0.0120 | 0.0020 | 0.0020 | 0.0020 | 0.0004 |

The equilibrium uptake for the above simplified example is 0.318 gram.

The following is the code in C language used to determine equilibrium uptake:

```c
/*                      takedata.c                         */
int take_data(int equil_samples,double equilibrium_constant)
{
double      delta;
static      double deltas[500];    /* table to store up to 500 deltas */
double      value;
double      prev_value;
clock_t     next_time;
int         i;
for (i=0; i<equil_samples; i++)
    deltas[i] = 9999.;             /* initialize all values in the delta
table to 9999. gms/sec */
delta_table_index = 0;             /* initialize where in the table to store
the next delta */
equilibrium_reached = 0;           /* initialize flag to indicate equilibrium
has not been reached */
next_time = clock();               /* initialize when to take the next
reading */
prev_reading = 0.;                 /* initialize the value of the previous
reading from the balance */
while (!equilibrium_reached) {     /* start of loop for
                                      checking for
equilibrium */
    next_time += 5000L;            /* calculate when to take
                                      next reading
*/
    while (clock() < next_time);   /* wait until 5
                                      seconds has elasped
from prev reading */
    value = get_balance_reading(); /* read the balance
                                      in grams */
    delta = fabs(prev_value − value)  /* calculate absolute
        / 5.0;                        value of flow in
last 5 seconds */
    prev_value = value;            /* store current
                                      value for next loop
*/
    deltas[delta table index] = delta;  /* store current
                                           delta value in the
                                           table of deltas */
    delta_table_index++;           /* increment pointer
                                      to next position
in table */
    if (delta_table_index ==
        equil_samples)             /* when the number of
                                      deltas = the
number of */
        delta_table_index = 0;     /* equilibrium samples
                                      specified, /*
                                   /* reset the pointer to the
                                      start of
the table. This way */
                                   /* the table always
                                      contains the last
xx current samples. */
    equilibrium_reached = 1;       /* set the flag
                                      to indicate
equilibrium is reached */
    for (i=0; i < equil_samples; i++)  /* check all the values
                                          in the delta
table */
        if (deltas[i] >= equilibrium_constant)  /* if any value is >
                                                   or = to the
equilibrium constant */
            equilibrium_reached = 0;   /* set the equlibrium
                                          flag to 0 (not
at equilibrium) */
    }                              /* go back to the start
                                      of the loop */
}
```

Capillary Sorption Parameters

Load Description (Confining Pressure): 0.2 psi load

Equilibrium Samples (n): 50

Equilibrium Constant: 0.0005 g/sec

Setup Height Value: 100 cm

Finish Height Value: 0 cm

Hydrostatic Head Parameters: 200, 180, 160, 140, 120, 100, 90, 80, 70, 60, 50, 45, 40, 35, 30, 25, 20, 15, 10, 5 and 0 cm.

The capillary sorption procedure is conducted using all the heights specified above, in the order stated, for the measurement of capillary sorption absorbent capacity. Even if it is desired to determine capillary sorption absorbent capacity at a particular height (e.g., 35 cm), the entire series of hydrostatic head parameters must be completed in the order specified. Although all these heights are used in performance of the capillary sorption test to generate capillary sorption isotherms for a test sample, the present disclosure describes the storage absorbent members in terms of their absorbent properties at specified heights of 200, 140, 100, 50, 35 and 0 cm.

Capillary Sorption Procedure
1) Follow the experimental setup procedure.
2) Make sure the temperature bath 208 is on and water is circulating through the glass frit 202 and that the glass frit disc 260 temperature is 31° C.
3) Position glass frit 202 at 200 cm suction height. Open stopcocks 209 and 210 to connect glass frit 202 with the balance liquid reservoir 206. (Stopcock 210 is closed to liquid reservoir 205.) Glass frit 202 is equilibrated for 30 minutes.
4) Input the above capillary sorption parameters into the computer.
5) Close stopcocks 209 and 210.
6) Move glass frit 202 to the set up height, 100 cm.
7) Place Teflon® ring 262 on surface of glass frit disc 260. Put O-ring 264 on Teflon® ring. Place pre-heated cylinder 266 concentrically on the Teflon® ring. Place test sample 270 concentrically in cylinder 266 on glass frit disc 260. Place piston 268 into cylinder 266. Additional confining weights are placed into piston chamber 290, if required.
8) Cover the glass frit 202 with apertured film.
9) The balance reading at this point establishes the zero or tare reading.
10) Move the glass frit 202 to 200 cm.
11) Open stopcocks 209 and 210 (stopcock 210 is closed to fluid reservoir 205) and begin balance and time readings.

Glass Frit Correction (blank correct uptake)

Since the glass frit disc 260 is a porous structure, the glass frit (202) capillary sorption absorption uptake (blank correct uptake) must be determined and subtracted to get the true test sample capillary sorption absorption uptake. The glass frit correction is performed for each new glass frit used. Run the capillary sorption procedure as described above, except without test sample, to obtain the Blank Uptake (g). The elapsed time at each specified height equals the Blank Time (s).

Evaporation Loss Correction
1) Move the glass frit 202 to 2 cm above zero and let it equilibrate at this height for 30 minutes with open stopcocks 209 and 210 (closed to reservoir 205).
2) Close stopcocks 209 and 210.
3) Place Teflon® ring 262 on surface of glass frit disc 260. Put O-ring 264 on Teflon® ring. Place pre-heated cylinder 266 concentrically on the Teflon® ring. Place piston 268 into cylinder 266. Place apertured film on glass frit 202.
4) Open stopcocks 209 and 210 (closed to reservoir 205) and record balance reading and time for 3.5 hours. Calculate Sample Evaporation (g/hr) as follows:

[balance reading at 1 hr–balance reading at 3.5 hr]/2.5 hr

Even after taking all the above precautions, some evaporative loss will occur, typically around 0.10 gm/hr for both the test sample and the frit correction. Ideally, the sample evaporation is measured for each newly installed glass frit 202.

Cleaning the Equipment

New Tygon® tubing 203 is used when a glass frit 202 is newly installed. Glass tubing 204 and 211, fluid reservoir 205, and balance liquid reservoir 206 are cleaned with 50% Clorox Bleach® in distilled water, followed by distilled water rinse, if microbial contamination is visible.

a. Cleaning after each experiment

At the end of each experiment (after the test sample has been removed), the glass frit is forward flushed (i.e., test liquid is introduced into the bottom of the glass frit) with 250 mL test liquid from liquid reservoir 205 to remove residual test sample from the glass frit disc pores. With stopcocks 209 and 210 open to liquid reservoir 205 and closed to balance liquid reservoir 206, the glass frit is removed front its holder, turned upside down and is rinsed out first with test liquid, followed by rinses with acetone and test liquid. During rinsing, the glass frit must be tilted upside down and rinse fluid is squirted onto the test sample contacting surface of the glass frit disc. After rinsing, the glass frit is forward flushed a second time with 250 ml synthetic urine. Finally, the glass frit is reinstalled in its holder and the frit surface is leveled.

b. Monitoring glass frit performance

Glass frit performance must be monitored after each cleaning procedure and for each newly installed glass frit, with the glass frit set up at 0 cm position. 50 ml of test liquid are poured onto the leveled glass frit disc surface (without Teflon® ring, O-ring and the cylinder/piston components). The time it takes for the test fluid level to drop to 5 mm above the glass frit disc surface is recorded. A periodic cleaning must be performed if this time exceeds 4.5 minutes.

c. Periodic cleaning

Periodically, (see monitoring frit performance, above) the glass frits are cleaned thoroughly to prevent clogging. Rinsing fluids are distilled water, acetone, 50% Clorox Bleach® in distilled water (to remove bacterial growth) and test liquid. Cleaning involves moving the glass frit from the holder and disconnecting all tubing. The glass frit is forward flushed (i.e., rinse liquid is introduced into the bottom of the glass frit) with the it upside down with the appropriate fluids and amounts in the following order:

1. 250 ml distilled water.
2. 100 ml acetone.
3. 250 ml distilled water.
4. 100 ml 50:50 Clorox®)/distilled water solution.
5. 250 ml distilled water.
6. 250 ml test fluid.

The cleaning procedure is satisfactory when glass frit performance is within the set criteria of fluid flow (see above) and when no residue is observable on the glass frit disc surface. If cleaning can not be performed successfully, the frit must be replaced.

Calculations

The computer is set up to provide a report consisting of the capillary suction height in cm, time, and the uptake in grams at each specified height. From this data, the capillary suction absorbent capacity, which is corrected for both the frit uptake and the evaporation loss, can be calculated. Also, based on the capillary suction absorbent capacity at 0 cm, the capillary absorption efficiency can be calculated at the specified heights. In addition, the initial effective uptake rate at 200 cm is calculated.

Blank Correct Uptake $$\text{Blank Correct Uptake (g)} = \text{Blank Uptake (g)} - \frac{\text{Blank Time (s)} * \text{Sample Evap. (g/hr)}}{3600 \text{ (s/hr)}}$$

Capillary Suction Absorbent Capacity ("CSAC")

$$CSAC(g/g) = \frac{Sample\ Uptake(g) - \frac{Sample\ Time(s) * Sample\ Evap.(g/hr)}{3600\ s/hr} - Blank\ Correct\ Uptake(g)}{Dry\ Weight\ of\ Sample(g)}$$

Initial Effective Uptake Rate at 200 cm ("IEUR")

$$IEUR(g/g/hr) = \frac{CSAC\ at\ 200\ cm(g/g)}{Sample\ Time\ at\ 200\ cm(s)}$$

Reporting

A minimum of 2 measurements should be taken for each test sample and the uptake averaged at each height to calculate capillary sorption absorbent capacity for a given storage absorbent member or a given high surface area material.

B. Vertical Hang Sorption Height (VHSH)

The Vertical Hang Sorption Height ("VHSH") test is effected by selecting a strip of foam of suitable length (typically at least 60 cm) with a width of typically about 1 cm. The strip is hung in a chamber thermostatted to 31° C. using clips to suspend the strip. The bottom of the strip is immersed in the test fluid, also at 31° C. The test fluid is preferably to synthetic urine as described in U.S. Pat. No. 5,599,335 (Goldman et al.) issued Feb. 4, 1997, the disclosure of which is incorporated by reference herein. Over time, the test fluid will wick up the strip and reach an equilibrium point where no further wicking occurs. The test fluid may be dyed to facilitate determination of the equilibrium point. Care must be taken to prevent evaporation from the sample, e.g. by encasing it within a glass tube wherein the glass does not touch the sample, and keeping the sample tube suitably capped. The time required to reach equilibrium may vary for the materials of this invention, and range from about 24 to 96 hrs, or more. When no perceptible change in the height of the wicking fluid is observed over a 1 hour period, equilibrium is assumed to have been achieved.

The test strip is removed from the test chamber with care to avoid expressing the fluid held therein. The strip is cut into 2.5 cm sections in length and each section is weighed. For convenience, the initial sections below about 50% of the fully expanded height may be cut into sections that are 2 inches (5.1 cm,. in length. These weights are divided by the oven dry weight of the foam to compute the capacity (g/g) at the various heights of the foam. A graph such as is depicted in FIG. 5 can be developed by charting the capacities vs. the heights at which the sections were taken. The VHSH height at X % is the height in cm where X% of the 0 cm capacity (or FAC) is retained in the foam. A typical value of importance is the VHSH at 90%. In principle, X may be any value. The most reproducible measure for VHSH is achieved at X=90%, within the experience of the inventors. It will be obvious to one skilled in the art that this single point value does not fully express the shape of the curve obtained in a plot of capacity vs. height The single point however serves as a practical point of comparison for the foams of the present invention.

VII. Representative Examples

EXAMPLE 1

Storage Absorbent Member Comprising Glass Microfibers

This example describes a high capillary suction absorbent member comprising hydrogel-forming absorbent polymer and high surface area glass micro fibers as formed using a wet end forming process for increased density and structural organization over conventional air deposition processes. In order to construct such a hydrogel-forming absorbent polymer containing member which approaches a homogeneous distribution of absorbent polymer in the glass micro fiber matrix, the following procedure is followed.

A mixture of 4.0 g of ASAP 2300 (available from Chemdal LTD, a subsidiary of American Colloid Co., Arlington Heights, Ill.; also available from The Procter & Gamble Co., Paper Technology Division, Cincinnati, Ohio) and 4.0 g of glass micro fiber (available as "Q-FIBERS, Code 108, 110 Bulk" from Manville Sales Corp., Denver, Colo.) are combined in an explosion resistant 3-gallon Commercial grade Warner blender with approximately 500 mL of 3A alcohol (95% ethanol, 5% methanol), or Isopropanol, or similar liquids which will not degrade nor absorb into the structure or composition of the involved polymers. The mixture is stirred on low speed for approximately 5 min. The mixture is poured into a 6 in.×6 in. "Paper Formation Box" with an 80 mesh Nylon Forming Wire (available from Appleton Mfg. Div., Productive Solutions, Inc., Neenah, Wis.) at the bottom of the upper portion of the Formation Box. Liquid level is brought to about 8 in. above the screen with addition of 3A alcohol, or appropriate solution. A paddle is used to mix the solution thoroughly in the top of the Formation box before liquid evacuation. A valve is opened below the forming wire and liquid is drained rapidly to ensure a uniform deposition on the forming wire. The screen is removed from the "Formation box", pulled across a vacuum source for removal of loosely held liquid, and allowed to air dry overnight in a desiccator containing a desiccant (such as DRIERITE, Sigme Chem. Co., St. Louis, Mo. 63178) to ensure uniform moisture content. Once dry, the absorbent member is removed from the forming screen.

A 5.4 cm cylindrical-shaped structure is arch punched from the member for measurement of capillary sorption absorbent capacity. Capillary sorption absorbent capacity data for the storage absorbent member is summarized in Table 1 below.

EXAMPLE 2

Preparation of High Surface Area Foam from a HIPE

A) HIPE Preparation

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (480 g), ditallow dimethyl ammonium methyl sulfate (80g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (53°–55° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 600 to its neighboring level with each level separated by 0.03 mm, each having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure of U.S. Pat. No. 5,827,909 (DesMarais), issued Oct. 27,1998, the disclosure of which is incorporated by reference herein. The Waukesha pump in the recirculation zone returns the minor portion to the entry point of the oil and water phase flow streams to the dynamic mixing zone.

The static mixer (TAH Industries Model 100-812) has 12 elements with a 1 in. (2.5 cm) outside diameter. A hose is mounted downstream from the static mixer to facilitate delivery of the emulsion to the device used for curing. Optionally an additional static mixer is used to provide addition back pressure to keep the hose filled. The optional static mixer can be a 1 in. (2.5 cm) pipe, 12 element mixer (McMaster-Carr, Aurora, Ohio, Model 3529K53).

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 cc/sec water phase.

Once the apparatus set-up is filled, agitation is begun in the dynamic mixer, with the impeller turning at 1750 RPM and recirculation is begun at a rate of about 30 cc/sec. The flow rate of the water phase is then steadily increased to a rate of 151.3 cc/sec over a time period of about 1 min., and the oil phase flow rate is reduced to 3.03 g/sec over a time period of about 3 min. The recirculation rate is steadily increased to about 150 cc/sec during the latter time period. The back pressure created by the dynamic zone and static mixers at this point is about 19.9 PSI (137 kPa), which represents the total pressure drop of the system. The Waukesha pump (Model 30) speed is then steadily decreased to a yield a recirculation rate of about 75 cc/sec.

B) Polymerization of HIPE

The HIPE flowing from the static mixer at this point is collected in a round polyethylene tub, 40 in. (102 cm) in diameter and 12.5 in. (31.8 cm) high, with removable sides, much like a springform pan used in cooking cakes. A pipe-like polyethylene insert 12.5 in. (31.8 cm) in diameter at its base is firmly affixed to the center of the base and is 12.5 in. (31.8 cm) high. The HIPE-containing tubs are kept in a room maintained at 65° C. for 18 hours to effect polymerization and form the foam.

C) Foam Washing and Dewatering

The cured HIPE foam is removed from the curing tubs. The foam at this point has residual water phase (containing dissolved emulsifiers, electrolyte, initiator residues, and initiator) about 48–52 times (48–52×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% $CaCl_2$ solution at 60° C., are squeezed in a series of 3 porous nip rolls equipped with vacuum to a water phase content of about 4×. The $CaCl_2$ content of the foam is between 8 and 10%.

The foam remains compressed after the final nip at a thickness of about 0.021 in. (0.053 cm). The foam is then dried in air for about 16 hours. Such drying reduces the moisture content to about 9–17% by weight of polymerized material. At this point, the foam sheets are very drapeable and "thin-after-drying".

EXAMPLE 3

Preparation of High Surface Area Foam from a HIPE

A) HIPE Preparation

The water and oil phase streams to be used in a continuous process for forming a HIPE emulsion is prepared according to Example 1. Separate streams of the oil phase (25° C.) and water phase (53°–55° C.) are fed to a dynamic mixing apparatus as detailed in Example 2.

Once the apparatus set-up is filled, agitation is begun in the dynamic mixer, with the impeller turning at 1700 RPM and recirculation is begun at a rate of about 30 cc/sec. The flow rate of the water phase is then steadily increased to a rate of 151.3 cc/sec over a time period of about 1 min., and the oil phase flow rate is reduced to 3.36 g/sec over a time period of about 3 min. The recirculation rate is steadily increased to about 150 cc/sec during the latter time period. The back pressure created by the dynamic zone and static mixers at this point is about 19.7 PSI (136 kPa), which represents the total pressure drop of the system. The Waukesha pump speed is then steadily decreased to a yield a recirculation rate of about 75 cc/sec.

B) Polymerization of HIPE

The HIPE flowing from the static mixer at this point is collected and cured into a polymeric foam as detailed in Example 2.

C) Foam Washing and Dewatering

The cured HIPE foam is removed from the curing tubs. The foam at this point has residual water phase (containing dissolved emulsifiers, electrolyte, initiator residues, and initiator) about 43–47 times (43–47×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% $CaCl_2$ solution at 60° C., are squeezed in a series of 3 porous nip rolls equipped with vacuum to a water phase content of about 4x. The $CaCl_2$ content of the foam is between 8 and 10%.

The foam remains compressed after the final nip at a thickness of about 0.028 in. (0.071 cm). The foam is then dried in air for about 16 hours. Such drying reduces the moisture content to about 9–17% by weight of polymerized material. At this point, the foam sheets are very drapeable and "thin-after-drying".

Capillary sorption absorbent capacity data for the storage member is summarized in Table 1 below.

EXAMPLE 4

Preparation of High Surface Area Foam from a HIPE

A) HIPE Preparation

The water and oil phase streams to be used in a Continuous process for forming a HIPE emulsion is prepared according to Example 2. Separate streams of the oil phase (25° C.) and water phase (53°–55° C.) are fed to a dynamic mixing apparatus as detailed in Example 1.

Once the apparatus set-up is filled, agitation is begun in the dynamic mixer, with the impeller turning at 1750 RPM and recirculation is begun at a rate of about 30 cc/sec. The flow rate of the water phase is then steadily increased to a rate of 151.3 cc/sec over a time period of about 1 min., and the oil phase flow rate is reduced to 3.78 g/sec over a time period of about 3 min. The recirculation rate is steadily increased to about 150 cc/sec during the latter time period. The back pressure created by the dynamic zone and static mixers at this point is about 18.7 PSI (129 kPa), which represents the total pressure drop of the system. The Waukesha pump speed is then steadily decreased to a yield a recirculation rate of about 75 cc/sec.

B) Polymerization of HIPE

The HIPE flowing from the static mixer at this point is collected and cured into a polymeric foam as detailed in Example 2.

C) Foam Washing and Dewatering

The cured HIPE foam is removed from the curing tubs. The foam at this point has residual water phase (containing dissolved emulsifiers, electrolyte, initiator residues, and initiator) about 38–42 times (38–42x) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6x) the weight of the polymerized material. At this point, the sheets are then resaturated with a 1.5% $CaCl_2$ solution at 60° C., are squeezed in a series of 3 porous nip rolls equipped with vacuum to a water phase content of about 4x. The $CaCl_2$ content of the foam is between 8 and 10%.

The foam remains compressed after the final nip at a thickness of about 0.028 in. (0.071 cm). The foam is then dried in air for about 16 hours. Such drying reduces the moisture content to about 9–17% by weight of polymerized material. At this point, the foam sheets are very drapeable and "thin-after-drying".

EXAMPLE 5

Storage Absorbent Member Comprising High Surface Area Polymeric Foam Material

This example describes a high capillary suction absorbent member comprising hydrogel-forming absorbent polymer and the high suction polymeric foam material prepared according to Example 3. In order to constrict a hydrogel-forming absorbent polymer containing member which approaches a relatively homogeneous distribution of absorbent polymer and polymeric foam, the following procedure is followed.

10 g of air dried polymeric foam (prepared according to Example 3 above) is placed in a blender (Osterizer model 848-36L) equipped with a 1.25 liter jar, into which 1 liter of 2% calcium chloride solution has been placed. After ensuring that all of the foam material is submerged, the blender is agitated on the 'Liquify' (high setting) for 10 seconds and then additionally agitated on the 'Grate' setting for 5 sec. The resultant slurry is then transferred to a Buchner funnel (Coors USA model 60283) lined with a paper towel. Approximately 500 ml of fluid is freely drained from the sample. The sample is then covered with a rubber membrane and vacuum is applied (approximately 500 mm Hg) to dewater the sample to a weight of 50 to 60 grams.

The aggregated sample is returned to a dry blender jar and dispersed with the agitation set on 'Liquify' while the jar and base are inverted and returned to upright several times to disperse the sample to approximately individual particles. The dispersed sample is then air dried under ambient conditions and then the foam particles are combined with hydrogel-forming absorbent polymer (ASAP 2300, available from Chemdal Corporation of Palantine, Ill.; also available from The Procter & Gamble Co., Paper Technology Division, Cincinnati, Ohio), to provide a storage absorbent member consisting of a homogeneous blend of 50%, by weight, hydrogel forming polymer and 50%, by weight, high surface area polymeric foam.

Capillary sorption absorbent capacity data for the storage absorbent member is summarized in Table 1 below.

EXAMPLE 6

Storage Absorbent Member Comprising High Surface Area Fibrets

This example describes a high capillary suction absorbent member comprising hydrogel-forming absorbent polymer and high surface area fibrets. High surface area fibrets, available from Hoechst Celanese Corp. (Charlotte, N.C.) as cellulose acetate Fibrets (, are combined with hydrogel-forming absorbent polymer (ASAP 2300, available from Chemdal Corporation of Palantine, Ill.; also available from The Procter & Gamble Co., Paper Technology Division, Cincinnati, Ohio), to provide a storage absorbent member consisting of a homogeneous blend of 50%, by weight, hydrogel-forming polymer and 50%, by weight, fibrets.

Capillary sorption absorbent capacity data for the storage absorbent member is summarized in Table 1 below.

TABLE 1

|  | CSAC* 0 cm (g/g) | CSAC* 35 cm (g/g) | CSAC* 70 cm (g/g) | CSAC* 120 cm (g/g) | CSAC* 200 cm (g/g) |
| --- | --- | --- | --- | --- | --- |
| Example 1 | 21.8 | 14.1 | 7.0 | 2.8 | 0.4 |
| Example 3 | 36.3 | 31.1 | 8.5 | 5.3 | 4.2 |
| Example 4 | 32.8 | 31.7 | 15.7 | 6.6 | 4.9 |
| Example 5 | 23.0 | 13.6 | 9.7 | 7.7 | 5.9 |
| Example 6 | 17.2 | 10.6 | 7.3 | 5.2 | 3.1 |
| Comp. A | 21.9 | 5.0 | 1.1 | 0.8 | 0.5 |
| Comp. B | 43.9 | 9.9 | 6.3 | 1.9 | 0.5 |

*CSAC = Capillary Sorption Absorbent Capacity

What is claimed is:

1. A high capillary suction storage absorbent member having a capillary sorption absorbent capacity at a height of 35 cm of at least about 12 g/g.

2. The absorbent member of claim 1 having a capillary sorption absorbent capacity at a height of 35 cm of at least about 14 g/g.

3. The absorbent member of claim 2 having capillary sorption absorbent capacity at a height of 35 cm of at least about 20 g/g.

4. The storage absorbent member of claim 1 having a capillary sorption absorbent capacity at a height of 35 cm of from about 12 g/g to about 60 g/g.

5. The storage absorbent member of claim 4 having a capillary sorption absorbent capacity at a height of 35 cm of from about 14 g/g to about 50 g/g.

6. The storage absorbent member of claim 5 having a capillary sorption absorbent capacity at a height of 35 cm of from about 20 g/g to about 40 g/g.

7. The storage absorbent member of claim 1 having a capillary sorption absorbent capacity at a height of 0 cm of at least about 15 g/g.

8. The storage absorbent member of claim 1 wherein the member comprises a collapsible polymeric foam structure having interconnected open-cells which, upon contact with aqueous fluids, can expand and absorb the fluids, the polymeric foam structure having an equilibrium 90% Vertical Hang Sorption Height (VHSH) of at least about 60 cm.

9. The storage absorbent member of claim 1 comprising osmotic absorbents and a discrete high surface area material, wherein the high surface area material is selected from the group consisting of high surface area fibers, a high surface area open-celled, hydrophilic polymeric foam, and mixtures thereof.

10. The storage absorbent member of claim 9 wherein the osmotic absorbent is a hydrogel-forming absorbent polymer.

11. The storage absorbent member of claim 10 wherein the high surface area material is an open-celled, hydrophilic polymeric foam in particulate form, the foam having a capillary sorption absorbent capacity at a height of 35 cm of at least about 5 g/g.

12. The absorbent member of claim 10 wherein the high surface area material comprises high surface area fibers having a capillary sorption absorbent capacity at a height of 35 cm of at least about 5 g/g.

13. An absorbent article comprising the storage absorbent member of claim 1.

14. A high capillary suction storage absorbent member having a capillary sorption absorbent capacity at a height of 70 cm of at least about 7 g/g.

15. The absorbent member of claim 14 having a capillary sorption absorbent capacity at a height of 70 cm of at least about 9 g/g.

16. The absorbent member of claim 15 having capillary sorption absorbent capacity at a height of 70 cm of at least about 11 g/g.

17. The absorbent member of claim 16 having a capillary sorption absorbent capacity at a height of 70 cm of at least about 14 g/g.

18. The storage absorbent member of claim 14 having a capillary sorption absorbent capacity at a height of 70 cm of from about 7g/g to about 35 g/g.

19. The storage absorbent member of claim 18 having a capillary sorption absorbent capacity at a height of 70 cm of from about 9 g/g to about 30 g/g.

20. The storage absorbent member of claim 19 having a capillary sorption absorbent capacity at a height of 70 cm of from about 11 g/g to about 25 g/g.

21. The storage absorbent member of claim 14 having a capillary sorption absorbent capacity at a height of 0 cm of at least about 11 g/g.

22. The storage absorbent member of claim 14 wherein the member comprises a collapsible polymeric foam structure having interconnected open-cells which, upon contact with aqueous fluids, can expand and absorb the fluids, the polymeric foam structure having an equilibrium 90% Vertical Hang Sorption Height (VHSH) of at least about 60 cm.

23. The storage absorbent member of claim 14 comprising osmotic absorbents and a discrete high surface area material, wherein the high surface area material is selected from the group consisting of high surface area fibers, a high surface area open-celled, hydrophilic polymeric foam, and mixtures thereof.

24. The storage absorbent member of claim 23 wherein the osmotic absorbent is a hydrogel-forming absorbent polymer.

25. The storage absorbent member of claim 24 where in the high surface area material is an open-celled, hydrophilic polymeric foam in particulate form, the foam having a capillary sorption absorbent capacity at a height of 70 cm of at least about 3 g/g.

26. The absorbent member of claim 24 wherein the high surface area material comprises high surface area fibers having a capillary sorption absorbent capacity at a height of 70 cm of at least about 3 g/g.

27. An absorbent article comprising the storage absorbent member of claim 14.

28. A high capillary suction storage absorbent member having a capillary sorption absorbent capacity at a height of 120 cm of at least about 4 g/g.

29. The absorbent member of claim 28 having a capillary sorption absorbent capacity at a height of 120 cm of at least about 5 g/g.

30. The absorbent member of claim 29 having capillary sorption absorbent capacity at a height of 120 cm of at least about 7 g/g.

31. The storage absorbent member of claim 28 having a capillary sorption absorbent capacity at a height of 120 cm of from about 4 g/g to about 29 g/g.

32. The storage absorbent member of claim 31 having a capillary sorption absorbent capacity at a height of 120 cm of from about 5 g/g to about 24 g/g.

33. The storage absorbent member of claim 32 having a capillary sorption absorbent capacity at a height of 120 cm of from about 7 g/g to about 19 g/g.

34. The storage absorbent member of claim 28 having a capillary sorption absorbent capacity at a height of 0 cm of at least about 15 g/g.

35. The storage absorbent member of claim 28 wherein the member comprises a collapsible polymeric foam structure having interconnected open-cells which, upon contact with aqueous fluids, can expand and absorb the fluids, the polymeric foam structure having an equilibrium 90% Vertical Hang Sorption Height (VHSH) of at least about 60 cm.

36. The storage absorbent member of claim 28 comprising osmotic absorbents and a discrete high surface area material, wherein the high surface area material is selected from the group consisting of high surface area fibers, a high surface area open-celled, hydrophilic polymeric foam, and mixtures thereof.

37. The storage absorbent member of claim 36 wherein the osmotic absorbent is a hydrogel-forming absorbent polymer.

38. The storage absorbent member of claim 37 wherein the high surface area material is an open-celled, hydrophilic polymeric foam in particulate form, the foam having a capillary sorption absorbent capacity at a height of 120 cm of at least about 2 g/g.

39. The absorbent member of claim 37 wherein the high surface area material comprises high surface area fibers having a capillary sorption absorbent capacity at a height of 120 cm of at least about 2 g/g.

40. An absorbent article comprising the storage absorbent member of claim 28.

41. A high capillary suction storage absorbent member having a capillary sorption absorbent capacity at a height of 200 cm of at least about 3 g/g.

42. The absorbent member of claim 41 having a capillary sorption absorbent capacity at a height of 200 cm of at least about 4 g/g.

43. The absorbent member of claim 42 having capillary sorption absorbent capacity at a height of 200 cm of at least about 6 g/g.

44. The storage absorbent member of claim 41 having a capillary sorption absorbent capacity at a height of 200 cm of from about 3 g/g to about 25 g/g.

45. The storage absorbent member of claim 44 having a capillary sorption absorbent capacity at a height of 200 cm of from about 4 g/g to about 20 g/g.

46. The storage absorbent member of claim 45 having a capillary sorption absorbent capacity at a height of 200 cm of from about 6 g/g to about 15 g/g.

47. The storage absorbent member of claim 41 having a capillary sorption absorbent capacity at a height of 0 cm of at least about 15 g/g.

48. The storage absorbent member of claim 41 wherein the member comprises a collapsible polymeric foam structure having interconnected open-cells which, upon contact with aqueous fluids, can expand and absorb the fluids, the polymeric foam structure having an equilibrium 90% Vertical Hang Sorption Height (VHSH) of at least about 60 cm.

49. The storage absorbent member of claim 41 comprising osmotic absorbents and a discrete high surface area material, wherein the high surface area material is selected from the group consisting of high surface area fibers, a high surface area open-celled, hydrophilic polymeric foam, and mixtures thereof.

50. The storage absorbent member of claim 49 wherein the osmotic absorbent is a hydrogel-forming absorbent polymer.

51. The storage absorbent member of claim 50 wherein the high surface area material is an open-celled, hydrophilic polymeric foam in particulate form, the foam having a capillary sorption absorbent capacity at a height of 200 cm of at least about 1 g/g.

52. The absorbent member of claim 50 wherein the high surface area material comprises high surface area fibers having a capillary sorption absorbent capacity at a height of 200 cm of at least about 1 g/g.

53. An absorbent article comprising the storage absorbent member of claim 41.

\* \* \* \* \*

UNITED STATES PATENT AND TRADEMARK OFFICE
CERTIFICATE OF CORRECTION

PATENT NO.    : 6,107,538
DATED         : August 22, 2000
INVENTOR(S)   : Young et al.

It is certified that error appears in the above-identified patent and that said Letters Patent is hereby corrected as shown below:

Column 1,
Line 26, please delete "member" and insert therefor -- members --.

Column 2,
Line 66, please delete "members" and insert therefor -- member's --.

Column 3,
Line 67, please delete "hand ling" and insert therefor -- handling --.

Column 5,
Line 12, after "disclosure" please insert "," (a comma).
Line 44, please delete "Frank-furt" and insert therefor -- Frankfurt --.

Column 6,
Line 4, please delete "ai" and insert therefor -- at --.
Line 7, please delete "cnm" and insert therefor -- cm --.
Line 65, after "g/g", please delete "," (the comma) and insert therefore -- ; -- (a semi-colon).

Column 9,
Line 13, after "area", please insert "." (a period).
Line 55, please delete "Care" and insert therefore -- Case --.

Column 10,
Line 52, after "temperature", please insert "." (a period).
Line 59, please delete "it" and insert therefor -- at --.
Line 61, please delete "-with" and insert therefor -- with --.

Column 12,
Line 28, please delete "::;et" and insert therefor -- set --.

Column 13,
Line 49, please delete "unction" and insert therefor -- function --.

Column 14,
Line 41, please delete "form" and insert therefor -- foam --.

Column 15,
Line 12, please delete "urines" and insert therefor -- urine --.
Line 48, please delete "cc-pending" and insert therefor -- co-pending --.
Line 49, after "Mar. 13,", please delete "998" and insert therefor -- 1998 --.

UNITED STATES PATENT AND TRADEMARK OFFICE
CERTIFICATE OF CORRECTION

PATENT NO. : 6,107,538
DATED : August 22, 2000
INVENTOR(S) : Young et al.

It is certified that error appears in the above-identified patent and that said Letters Patent is hereby corrected as shown below:

Column 18,
Line 5, please delete "a so" and insert therefor -- also --.
Lines 19-20, please delete "09/00,918" and insert therefor -- 09/003,918 --.

Column 19,
Line 11, please delete "50 Mm" and insert therefor -- 50$\mu$m --.
Line 29, after "1987", please delete "." (the period) and insert therefor -- , -- (a comma).

Column 20,
Line 16, please delete "50" and insert therefor -- 5% --.

Column 22,
Line 10, after "g/g", please delete "," (the comma) and insert therefor -- ; -- (a semi-colon).
Line 13, after "g/g", please delete "," (the comma) and insert therefor -- ; -- (a semi-colon).
Line 19, after "preferably" please delete "," (the comma).
Line 46, please delete "b)y" and insert therefor -- by --.
Line 64, after "area" (first occurrence), please insert "." (a period), a carriage return and indent for a new paragraph starting with the word "High".

Column 23,
Line 60, please delete "material;" and insert therefor -- materials --.

Column 25,
Line 25, please delete "93%" and insert therefor -- 98% --.
Line 31, after "member", please delete "," (the comma) and insert therefor -- ; -- (a semi-colon).

Column 26,
Line 43, please delete "ally" and insert therefor -- any --.

Column 27,
Line 2, please delete "halve" and insert therefor -- have --.
Line 59, please delete "al)out" and insert therefor -- about --.

Column 28,
Line 4, please delete "aid" and insert therefor -- and --.
Line 62, please delete "general y" and insert therefor -- generally --.

Column 31,
Line 47, please delete "tie" and insert therefor -- the --.

UNITED STATES PATENT AND TRADEMARK OFFICE
CERTIFICATE OF CORRECTION

PATENT NO.   : 6,107,538
DATED        : August 22, 2000
INVENTOR(S)  : Young et al.

It is certified that error appears in the above-identified patent and that said Letters Patent is hereby corrected as shown below:

Column 32,
Line 39, please delete "081825,071" and insert therefor -- 08/825,071 --.
Line 39, please delete "La Von" and insert therefor -- LaVon --.

Column 33,
Line 4, please delete "carted" and insert therefor -- carded --.
Line 6, after "art", please insert "." (a period).

Column 35,
Line 16, please delete "La Von" and insert therefor -- LaVon --.
Line 44, after "WA" please delete "." (the period).

Column 37,
Line 28, please delete "io" and insert therefor -- to --.
Line 35, please delete "tenet" and insert therefor -- test --.
Line 52, please delete "rain" and insert therefor -- drain --.
Line 54, after "206", please delete "." (the period).
Lines 55-56, please delete "light weight" and insert therefor -- lightweight -- (one word).

Column 38,
Line 30, please delete "flitted" and insert therefor -- fritted --.
Line 48, please delete "AS563A" and insert therefor -- AS568A --.

Column 39,
Line 2, please delete "ani" and insert therefor -- an --.
Line 34, please delete "or" (second occurrence), and insert therefor -- of --.

Column 40,
Lines 10 and 32, please delete "flit" and insert therefor -- frit --.
After Line 1, please insert the following:

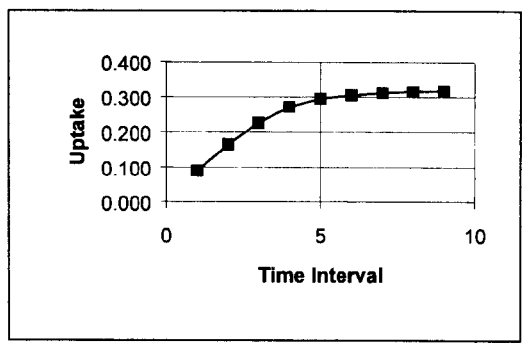

UNITED STATES PATENT AND TRADEMARK OFFICE
CERTIFICATE OF CORRECTION

PATENT NO. : 6,107,538
DATED : August 22, 2000
INVENTOR(S) : Young et al.

It is certified that error appears in the above-identified patent and that said Letters Patent is hereby corrected as shown below:

Column 44,
Line 4, please delete "front" and insert therefor -- from --.
Line 30, please delete "moving" and insert therefor -- removing --.

Column 45,
Line 21, please delete "i s" and insert therefor -- is --.
Line 58, after "height", please insert "." (a period).

Column 47,
Line 17, please delete "600" and insert therefor -- 60° --.
Line 27, after "Oct. 27,", please insert a space.

Column 50,
Line 2, please delete "constrict" and insert therefor -- construct --.

Column 52,
Line 3, please delete "11 g/g" and insert therefor -- 15 g/g --.

Signed and Sealed this

Twenty-seventh Day of September, 2005

JON W. DUDAS
*Director of the United States Patent and Trademark Office*